United States Patent
Zhou et al.

(10) Patent No.: US 10,639,255 B2
(45) Date of Patent: *May 5, 2020

(54) NAIL TREATMENT SYSTEM

(71) Applicant: L'OREAL, Paris (FR)

(72) Inventors: XianZhi Zhou, Millburn, NJ (US); Chunhua Li, Hillsborough, NJ (US); Hy Si Bui, Piscataway, NJ (US); Jean-Thierry Simonnet, Rueil Malmaison (FR); Carl Riachi, Paris (FR); Guillaume Kergosien, Chaville (FR)

(73) Assignee: L'OREAL, Paris (FR)

( * ) Notice: Subject to any disclaimer, the term of this patent is extended or adjusted under 35 U.S.C. 154(b) by 359 days.

This patent is subject to a terminal disclaimer.

(21) Appl. No.: 14/573,918

(22) Filed: Dec. 17, 2014

(65) Prior Publication Data

US 2016/0175212 A1    Jun. 23, 2016

(51) Int. Cl.
| | | |
|---|---|---|
| *A61K 8/42* | (2006.01) | |
| *A61Q 3/00* | (2006.01) | |
| *A61K 8/87* | (2006.01) | |
| *A61Q 3/02* | (2006.01) | |
| *A61K 8/81* | (2006.01) | |
| *A61K 8/35* | (2006.01) | |
| *A61K 8/36* | (2006.01) | |

(52) U.S. Cl.
CPC .................. *A61K 8/42* (2013.01); *A61K 8/35* (2013.01); *A61K 8/36* (2013.01); *A61K 8/8147* (2013.01); *A61K 8/8152* (2013.01); *A61K 8/87* (2013.01); *A61Q 3/00* (2013.01); *A61Q 3/02* (2013.01); *A61K 2800/43* (2013.01); *A61K 2800/81* (2013.01); *A61K 2800/88* (2013.01); *A61K 2800/884* (2013.01); *A61K 2800/95* (2013.01)

(58) Field of Classification Search
None
See application file for complete search history.

(56) References Cited

U.S. PATENT DOCUMENTS

| | | | | |
|---|---|---|---|---|
| 3,928,113 | A * | 12/1975 | Rosenberg | A61K 8/87 132/73 |
| 4,126,144 | A * | 11/1978 | Duarte | A45D 29/001 132/73 |
| 5,683,681 | A * | 11/1997 | Ramin | A61K 8/44 424/401 |
| 6,306,375 | B1 * | 10/2001 | Ellingson et al. | 424/61 |
| 6,391,964 | B1 * | 5/2002 | Tartaglia | A61K 8/8152 206/568 |
| 2004/0180032 | A1 * | 9/2004 | Manelski et al. | 424/70.121 |
| 2011/0256079 | A1 * | 10/2011 | Kozachek | 424/61 |
| 2012/0103354 | A1 * | 5/2012 | Park | 132/200 |
| 2015/0007846 | A1 * | 1/2015 | Weiburg | A61Q 3/02 132/200 |

FOREIGN PATENT DOCUMENTS

WO    WO 2013192515 A1 * 12/2013

OTHER PUBLICATIONS

Guyot et al. Progress in Polymer Science 2002 27:1573-1615 (Year: 2002).*

* cited by examiner

*Primary Examiner* — Robert A Wax
*Assistant Examiner* — Caralynne E Helm
(74) *Attorney, Agent, or Firm* — Oblon, McClelland, Maier & Neustadt, L.L.P.

(57) ABSTRACT

The invention relates to nail treatment system comprising at least one basecoat, at least one second coat, and optionally at least one topcoat, wherein the basecoat comprises water and at least one non-UV curable adhesive latex compound, and the second coat comprises at least one photocrosslinkable urethane (meth)acrylate and at least one (meth)acrylate monomer.

16 Claims, No Drawings

NAIL TREATMENT SYSTEM

FIELD OF THE INVENTION

The present invention relates to a nail treatment system comprising at least one basecoat, at least one second coat and optionally at least one topcoat, wherein basecoat comprises water and at least one non-UV curable adhesive latex and the second coat comprises at least one photocrosslinkable urethane (meth)acrylate and at least one (meth)acrylate monomer. Owing to the unique properties of the basecoat and the second coat, this nail composition system can be easily removed, leaving nails looking healthy, without sacrificing wear.

DISCUSSION OF THE BACKGROUND

Traditional nail enamel can contain a large amount of nitrocellulose, primarily because nitrocellulose provides good adhesion of the compositions to nails upon application. Such conventional nail polish compositions (with or without nitrocellulose) require solvent-based removal products to remove them from nails. However, it is desirable to avoid such solvent-based removers, both, from a personal perspective (to avoid damage to nails) and an environmental perspective (to avoid damage to the environment).

Other types of nail polish compositions exist. For example, UV (ultraviolet) gel compositions are known. UV gel compositions typically consist but are not limited to a layer of basecoat for adhesion to the nails, two color coats to enhance the color and one topcoat for shine and durability. Each layer of each coat needs to be cured (polymerized) with a UV or LED Lamp. Such polymerizable compositions have been described for example in U.S. Pat. No. 7,375,144 and WO2014/086875 the entire contents of which are hereby incorporated by reference.

The adhesion of UV gel nail compositions to the nail surface and cohesive force between the layers of multiple UV gel treatment is so strong that it is difficult to remove such compositions from nails. To remove such UV gel products from nails, it is usually required to soak nails with a harsh solvent such as acetone for at least 10 minutes or more to effect removal. Frequent and/or prolonged use of such solvents in this manner can damage nails such as, for example, by making them dry and brittle. At the same time, the removal process is time-consuming.

In the past, proposed solutions to improve the removal of UV gel nail compositions have focused on altering the composition of the UV gel layers themselves, for example by including additives which are soluble in solvents like acetone, ethyl acetate, butyl acetate, etc. to the layers. For instance, US2011082228A, US2011081306A, US2011060065A, US2011182838A, US2011182838A and US2011274633A relate to the use of a non-reactive, solvent-dissolvable polymer such as cellulose acetate butyrate, cellulose acetate propionate, and mixtures to enhance removal properties. Adding such non-reactive, solvent-dissolvable compounds improves saturation of the coatings by solvent and hence can speed up the removal process. The speed of removal depends on the type and the quantity of additives introduced in the composition. However, the use of solvent to remove the composition is still required.

Another proposed solution to improve removal of UV gel nail compositions is described in WO2014/088570 and WO2014/028021. These publications disclose the use of a water-based basecoat composition (primer) prior to the application of UV gel color coat(s) and/or UV gel topcoat, thereby allowing easy removal of all coats with the use of water. However, such nail applications have poor wear.

There remains a need for UV gel compositions that are safe, adhere well to nails and can be easily and quickly removed with minimum damage to nails.

The inventive nail treatment system provides the unique combination of basecoat containing a non-UV curable adhesive latex with a second coat (which preferably is a color coat) containing both photocrosslinkable urethane (meth)acrylates oligomers and (meth)acrylate monomers. The inventive nail treatment system optionally may also include a third or "topcoat" which optionally may also include photocrosslinkable urethane (meth)acrylates oligomers and (meth)acrylate monomers. The compositions of the invention deliver very strong adhesion to the nail and good wear, while at the same time the treatment system can be easily removed with the use of warm, soapy water.

Without being bound by theory, it is believed that (meth)acrylate monomers which are characterized as good adhesion promoters having excellent solvency power, improve adhesion between the basecoat and the second coat (which preferably is the color coat). Due to their capability of being powerful solvents, they partially solubilize and at the same time penetrate the basecoat of the inventive system which increases adhesion. Simultaneously, the photocrosslinkable urethane (meth)acrylates present in the inventive color/topcoat improve removability of said nail treatment system due to formation of a very strong and cohesive film which can be peeled off from the nail surface as a whole piece.

Furthermore, the presence of non-UV curable adhesive latex in the basecoat composition additionally enhances the removability of the inventive treatment system from the nails. Because the non-UV curable latex is hydrophilic, its exposure to warm and soapy water results in swelling. This results in decreased of adhesion between nails and the second and top coats of the inventive nail treatment system. The reduced adhesion force allows for easy peeling of the inventive nail treatment from the nail surface. Starting from the free edge of the nail, the consumer can easily remove the treatment system of inventive compositions.

As per this invention, the removal method of the nail treatment system does not require the use of harsh for nails, organic solvent, just warm and soapy water.

SUMMARY OF THE INVENTION

The present invention relates to a nail treatment system comprising:
(1) at least one basecoat comprising:
  water; and
  at least one non-UV curable latex; and
(2) at least one second coat comprising:
  at least one photocrosslinkable urethane (meth)acrylate compound P1;
  at least one photocrosslinkable (meth)acrylate monomer; and at least one photoinitiator.

Another aspect of the present invention relates to a nail treatment system comprising at least one basecoat preferably further comprising at least one compound selected from at least one plasticizer, at least one coalescent, at least one abrasive agent, and mixtures thereof.

In another embodiment, the present invention relates to a nail treatment system comprising at least one second coat preferably further comprising at least one compound selected from at least one photocrosslinkable urethane (meth)acrylate compound P2, at least one film-forming polymer P3, at least one coloring agent, at least one solvent, and mixtures thereof.

Another aspect of the present invention relates to methods for making up and/or protecting nails comprising applying to the nails (1) at least one basecoat as defined above, (2) at least one second coat as defined above, and (3) optionally at least one topcoat as further defined. In a preferred embodiment the second coat is a color coat.

In another embodiment, the present invention relates to methods of removing a nail treatment system comprising: applying to the nails (1) at least one basecoat as defined above, (2) at least one second coat as defined above, and (3) optionally at least one topcoat as further defined, and removing the applied compositions from the nails by their exposure to water and peeling them off the nails.

It is to be understood that both the foregoing general description and the following detailed description are exemplary and explanatory only, and are not restrictive of the invention.

DETAILED DESCRIPTION OF THE INVENTION

In the following description of the invention and the claims appended hereto, it is to be understood that the terms used have their ordinary and accustomed meanings in the art, unless otherwise specified.

"About" as used herein means within 10% of the indicated number (e.g. "about 10%" means 9%-11% and "about 2%" means 1.8%-2.2%).

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

"Abrasive" or "surface disrupting agent" means a rough material causing disruption of a surface and increase the roughness of the surface to improve adhesion between a surface and a coating.

"Adhesion" as used herein, refers to chemical and/or physical bonding between a coating and a substrate. Good adhesion between nail polish and nail surface should translate to good wear properties on consumers. Adhesion properties can be quantified by in-vitro method such as a cross-cut adhesion test. In the test, a lattice pattern is cut into the coating and penetrates through to the substrate. A pressure sensitive tape is applied to the sample and then pulled off. The adhesion property can be quantified by the area of the coating remaining after peeling. For example, if the whole film remains after peeling, it indicates excellent adhesion. If most of the film gets peeled off, it indicates poor adhesion. The cross-cut test is an industrial standard test for testing adhesion for coatings. (Reference # ISO/DIN 2409, ASTM D3359).

"Easy removal" means the composition may be substantially removed with a non-harsh remover, such as water and/or with a water-based cleansing solution, and without excessive rubbing.

"Film former", "film-forming polymer" or "film forming agent" as used herein means a polymer or resin that leaves a film on the substrate to which it is applied, for example, after a solvent accompanying the film former has evaporated, absorbed into and/or dissipated on the substrate.

"Free" or "devoid" of as it is used herein means that while it is preferred that no amount of the specific component be present in the composition, it is possible to have very small amounts of it in the compositions of the invention provided that these amounts do not materially affect at least one, preferably most, of the advantageous properties of the compositions of the invention. Thus, for example, "free of solvents" means that non-aqueous solvents are preferably omitted (that is 0% by weight), but can be present in the composition at an amount of less than about 0.25% by weight, typically less than about 0.1% by weight, typically less than about 0.05% by weight, based on the total weight of the composition as a whole.

"Solvency power" means the ability to dissolve other substances.

"Makeup Result" as used herein, refers to compositions where color remains the same or substantially the same as at the time of application, as viewed by the naked eye, after an extended period of time. "Makeup Result" may be evaluated by evaluating long wear properties by any method known in the art for evaluating such properties. For example, long wear may be evaluated by a test involving the application of a composition to nails and evaluating the color of the composition after an extended period of time. For example, the color of a composition may be evaluated immediately following application to nails and these characteristics may then be re-evaluated and compared after a certain amount of time. Further, these characteristics may be evaluated with respect to other compositions, such as commercially available compositions.

"(Meth)acrylate monomer" or "ethylenically unsaturated monomer" refers to a compound comprising a single (meth) acrylate function according to the formula $H_2C=C(R)-C(O)-O-$, where $R=H$ or $CH_3$ capable of reacting with other molecules.

"Nails", "fingernail or "toenail" refers to a human keratinous substrate which can be treated (decorated) with a single or multiple nail cosmetic compositions.

"Nail treatment system" means multiple compositions applied on the surface of nails.

"Non-photocrosslinkable compound" refers to a compound inert to any light exposure i.e. that does not polymerize and/or is not crosslinked.

"Non-UV curable" means a substance which does not require exposure to UV light in order to have cross-linking polymer chains.

"Oligomer" refers to a compound comprising at least two (meth)acrylate functions.

"Photocrosslinkable compound" refers to an organic compound suitable for crosslinking under the action of a light ray, resulting in a crosslinked polymer network.

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The compositions and methods of the present invention can comprise, consist of, or consist essentially of the essential elements and limitations of the invention described herein, as well as any additional or optional ingredients, components, or limitations described herein or otherwise useful.

In another embodiment, invention relates to a nail treatment system comprising:

(1) at least one basecoat as defined above; and
(2) at least one second coat comprising:
  at least one photocrosslinkable urethane (meth)acrylate compound P1 comprising at least one structural unit:

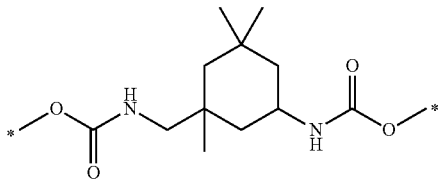

at least one photocrosslinkable urethane (meth)acrylate compound P2, comprising at least one polyethylene glycol chain;
  at least one (meth)acrylate monomer;
  at least one photoinitiator;
  optionally at least one film-forming polymer P3;
  optionally at least one coloring agent; and
  optionally at least one solvent;
  wherein the ratio of at least one photocrosslinkable urethane (meth)acrylate compound P1 to the at least one (meth)acrylate monomer is greater than or equal to about 1:1. In a preferred embodiment, the ratio of at least one photocrosslinkable urethane (meth)acrylate compound P1 to the at least one methacrylate monomer is between about 1.5:1 and about 5:1, more preferably between about 2:1 and about 4:1, by weight, relative to the total weight of the composition.

In another embodiment, the invention relates to a nail treatment system comprising:
(1) at least one basecoat as defined above;
(2) at least one second coat as defined above; and
(3) at least one topcoat comprising:
  at least one photocrosslinkable urethane (meth)acrylate compound P1 comprising at least one structural unit:

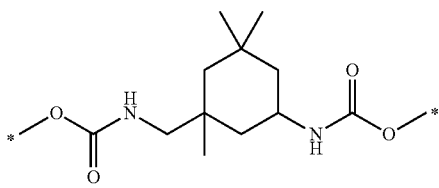

at least one photocrosslinkable urethane (meth)acrylate compound P2 comprising at least one polyethylene glycol chain;
  at least one film-forming polymer P3;
  at least one (meth)acrylate monomer;
  at least one photoinitiator;
  optionally at least one coloring agent; and
  optionally at least one solvent;
  wherein the ratio of at least one photocrosslinkable urethane (meth)acrylate compound P1 to at least one (meth)acrylate monomer is greater than or equal to about 1:1. In a preferred embodiment, the ratio of at least one photocrosslinkable urethane (meth)acrylate compound P1 to the at least one methacrylate monomer is between about 1.5:1 and about 5:1, more preferably between about 2:1 and about 4:1, by weight, relative to the total weight of the composition.

In another embodiment, the invention relates to a nail treatment system comprising:
(1) at least one basecoat coat comprising:
  water present in an amount from about 30% to about 90% by weight;
  at least one non-UV curable adhesive latex in an amount from about 5% to about 100% by weight;
  optionally at least one plasticizer in an amount from about 1% to about 10% by weight;
  optionally at least one coalescent in an amount from about 1% to about 20% by weight; and
  optionally at least one abrasive agent in an amount from about 0.1% to about 5% by weight; and
(2) at least one second coat comprising:
  at least one photocrosslinkable urethane (meth)acrylate compound P1 comprising at least one structural unit:

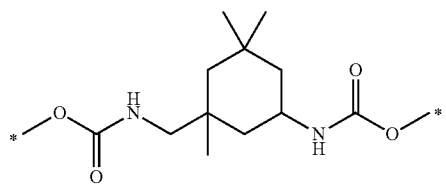

in an amount from about 5% to about 80% by weight;
  at least one (meth)acrylate monomer in an amount from about 5% to about 30% by weight;
  at least one photoinitiator in an amount from about 1% to about 10% by weight;
  optionally at least one photocrosslinkable urethane (meth)acrylate compound P2 in an amount from about 5% to about 70% by weight;
  optionally at least one film-forming polymer P3 in an amount from about 0.2% to about 10% by weight;
  optionally at least one coloring agent in an amount from about 0.1% to about 5% by weight; and
  optionally at least one solvent from about 0.5% to about 10% by weight;
  wherein the ratio of at least one photocrosslinkable urethane (meth)acrylate compound P1 to at least one (meth)acrylate monomer is greater than or equal to about 1:1. In a preferred embodiment the ratio of at least one photocrosslinkable urethane (meth)acrylate compound P1 to at least one methacrylate monomer is between about 1.5:1 and about 5:1, more preferably is between about 2:1 and about 4:1, by weight, relative to the total weight of the composition; and
(3) optionally at least one topcoat as defined above.

The present invention also relates to a kit for a nail treatment system comprising (1) at least one basecoat as defined above, (2) at least one second coat as defined above and (3) optionally at least one topcoat as defined above.

Preferably, the kit for a nail composition system further comprises instructions for removing a nail composition system by removing the basecoat composition to effect removal of the nail composition set.

Nail Treatment System (Nail Composition System)

According to the present invention, a nail treatment system comprising at least one basecoat and at least one second coat (color coat) composition is described. The nail treatment system of the present invention can optionally further comprises at least one topcoat.

It should be understood that each coat in the nail treatment system, itself, can comprise one or more layers of each composition. Thus, the at least one basecoat can comprise one or more basecoat layers; the at least second coat (color coat) can comprise one or more second coat (color coat) layers; the at least one topcoat can comprise one or more topcoat layers. Preferably, each basecoat, second coat (color coat) and topcoat compositions contain three or fewer layers of compositions, more preferably two or fewer layers of compositions, and most preferably a single layer of compositions.

According to the present invention, the basecoat comprises water and at least one adhesive compound, such as water-dispersed non-UV curable latex or pseudolatex. During removal, the basecoat allows an applied nail composition (UV Gel composition) to be easily peeled off after exposure of the whole nail treatment system to warm water, preferably without exposure to further solvents or treatments.

According to the present invention, the basecoat, second coat (color coat) and topcoat of the nail treatment system can be any suitable composition for application to nails. For example, the basecoat(s) can be an adhesive layer or an undercoat layer; the second coat(s) can be a nail polish composition(s) such as, for example, a UV gel composition; the topcoat(s) can be a shine layer and/or a protective layer.

During application of the nail treatment system, the basecoat is applied to the nail. Then, the second coat (color coat) is applied to the basecoat. Then, optionally a topcoat is applied over the second coat.

Basecoat

According to the present invention, a basecoat composition for application to nails is provided. In accordance with the present invention, the basecoat comprises:
water;
at least one non-UV curable latex adhesive, such as water-dispersed non-UV curable latex or pseudolatex;
optionally at least one plasticizer;
optionally at least one coalescent; and
optionally at least one abrasive agent.

As per another aspect of the present invention, a basecoat composition is non-UV curable composition.

During use, the basecoat allows a nail composition comprising a nail polish (UV Gel composition) to be easily peeled off. Preferably, the nail composition system can be peeled off in whole pieces.

As explained above, the nail composition system is applied to nail(s) such that the order is: nail/basecoat/second coat (color coat)/topcoat (optional).

During removal, the basecoat is preferably peeled off from the edge of the nail. Such removal of the nail composition is easy and quick (time efficient), and can be performed without the aid of solvent-based (non-water) removers (although such removers can be used to aid in removal, if desired).

The speed of removal of the nail composition can be increased by dipping nail(s) having an applied nail composition into warm water prior to peeling. "Warm water" is defined herein as water above room temperature such as, for example, water at 26° C.-60° C., preferably at 30° C.-6° C., including all ranges and subranges there between.

Water and Other Solvents

The basecoat compositions of the invention also comprise water in an amount ranging from about 10% to about 95%, preferably from about 20% to about 85%, most typically from about 30% about 65%, including all ranges and subranges therebetween, by weight, relative to the total weight of the compositions.

The compositions of the invention may include additional solvents. In particular, the aqueous phase may include at least one organic solvent that is water dispersible. Non-limiting examples of suitable organic solvents include $C_{1-4}$ alkanols such as ethanol and isopropanol, glycerol, glycols such as 2-butoxyethanol, propylene glycol, butylene glycol, aromatic alcohols such as benzyl alcohol and phenoxyethanol; analogous products and mixtures of the foregoing products.

Other solvents include caprylic/capric acid triglycerides (such as those sold under the trade name Miglyol®).

In addition to water, the compositions of the invention may comprise a solvent in an amount ranging from about 0.1% to about 20%, preferably from about 1% to about 10%, including all ranges and subranges therebetween, by weight, relative to the total weight of the compositions.

Non-UV Curable Adhesives

As indicated above, the basecoat comprises non-UV curable adhesive compounds. The non-UV curable adhesive compounds include but are not limited to latex or pseudolatex. Latex and pseudolatex are colloidal dispersions of polymer particles in an aqueous liquid phase.

"Latex" is generally obtained by suspension or emulsion polymerization or copolymerization of monomers according to processes that are well known to those of ordinary skill in the art. Such monomers may be chosen in particular from styrene, butadiene, acrylonitrile, chloroprene, vinyl acetate, urethanes, isoprene, isobutylene, and acrylic or methacrylic acid, maleic acid, crotonic acid or itaconic acid or esters or amides thereof.

"Pseudolatex" denotes a dispersion consisting of generally spherical particles of a polymer, these particles being obtained by dispersing the polymer in a suitable aqueous phase.

Latex and pseudolatex have film-forming properties that are advantageous for imparting adhesive properties to the nails. That is, latex and pseudolatex aid in adhering the basecoat and, thus, the nail composition to the nail.

Specific examples of types of latexes and pseudolatexes as well as specific examples of latexes and pseudolatexes include:
Synthetic polymers of the polycondensate type or of the free-radical type;
Acrylic polymers resulting from the copolymerization of monomers chosen from the esters and/or amides of acrylic acid or of methacrylic acid. As examples of monomers of ester type, mention may be made of methyl methacrylate, ethyl methacrylate, butyl methacrylate, isobutyl methacrylate, 2-ethylhexyl methacrylate and lauryl methacrylate. As examples of monomers of amide type, mention may be made of N-t-butylacrylamide and N-t-octylacrylamide.
Acrylic polymers obtained by copolymerization of ethylenically unsaturated monomers containing hydrophilic groups, preferably of nonionic nature, such as hydroxyethyl acrylate, 2-hydroxypropyl acrylate, hydroxyethyl methacrylate and 2-hydroxypropyl methacrylate;
Vinyl polymers resulting from the homopolymerization or copolymerization of monomers chosen from vinyl esters, styrene or butadiene. As examples of vinyl esters, mention may be made of vinyl acetate, vinyl neodecanoate, vinyl pivalate, vinyl benzoate and vinyl t-butylbenzoate.

Acrylic/Silicone Copolymers;
Polymers resulting from the free-radical polymerization of one or more free-radical monomers inside and/or partially at the surface of preexisting particles of at least one polymer chosen from the group consisting of polyurethanes, polyureas, polyesters, polyesteramides and/or alkyds. These polymers are generally referred to as "hybrid polymers"; and bimodal film forming agents which form a bimodal interpenetrating network containing multiple functionalities (for example, cationic and anionic functionalities) which is reversibly cross-linked at least partially through the multiple functionalities are disclosed in PCT patent application nos. WO 05/087191 and WO 06/028931, and corresponding U.S. provisional application Nos. 60/551,658, 60/606,985, and 60/627,224, the entire contents of all of which are hereby incorporated by reference in their entirety. Suitable bimodal film forming agents include, but are not limited to, film forming agents having both cationic and anionic functionalities. According to particularly preferred embodiments of the present invention, the bimodal film forming agent comprises at least one acrylic acid-based, (meth)acrylic acid-based, acrylate-based or (meth)acrylate-based monomer having anionic and/or cationic functionalities. Suitable polymers or copolymers include, but are not limited to, polymers comprising polyacrylates such as those identified in the International Cosmetic Ingredient Dictionary and Handbook (9.sup.th ed. 2002) such as, for example, polyacrylate-1, polyacrylate-2, polyacrylate-3, polyacrylate-4, polyacrylate-16, polyacrylate-17, polyacrylate-18, polyacrylate-19, etc. Such (co)polymers, or similar (co)polymers, can be combined individually or with other (co)polymers in such a way to form suitable bimodal film forming agents having both cationic and anionic functionalities. According to particularly preferred embodiments, the bimodal film forming agent is selected from the group consisting of polymers consisting of polyacrylate-21 and acrylates/dimethylaminoethylmethacrylate copolymer (marketed under the name Syntran PC 5100 by Interpolymer), polyacrylate-16 (marketed under the name Syntran PC 5112 by Interpolymer), polyacrylate-18 and polyacrylate-19 (marketed under the name Syntran PC 5107 by Interpolymer), and polyacrylate-18 and polyacrylate-1 g (marketed under the name Syntran PC 5117 by Interpolymer). The bimodal film forming agent containing polyacrylate-21 and acrylates/dimethylaminoethylmethacrylate copolymer (Syntran PC 5100) and polyacrylate-16 (Syntran PC 5112) are particularly preferred.

Representative examples of suitable latexes include acrylic copolymer dispersions sold under the names Neocryl XK-90® (INCI name: acrylic/styrene copolymer), Neocryl A-1070® (INCI name: acrylic/styrene copolymer), Neocryl A-1090® (INCI name: acrylic/styrene copolymer), Neocryl BT-62® (INCI name: acrylic/styrene copolymer), Neocryl A-1079® (INCI name: acrylic/styrene copolymer) and Neocryl A-523® (INCI name: acrylic/styrene copolymer) by the company Avecia-Neoresins, Dow Latex 432® (INCI name: Styrene/Acrylates Copolymer) by the company Dow Chemical, Daitosol 5000 AD® (INCI name: acrylates copolymer) by the company Daito Kasey Kogyo; or the aqueous dispersions of polyurethane sold under the names Neorez R-981® (INCI name: polyester-polyurethane copolymer) and Neorez R-974® (INCI name: polyester-polyurethane copolymer) by the company Avecia-Neoresins, Avalure UR-405® (INCI name: polyurethane-2), Avalure UR-410® (INCI name: polyurethane-2), Avalure UR-425° (INCI name: polyurethane-2), Avalure UR-450® (INCI name: PPG-17/IPDI/DMPA copolymer), Sancure 875® (INCI name: polyester-polyurethane copolymer), Sancure 861® (INCI name: polyester-polyurethane copolymer), Sancure 878® (INCI name: polyester-polyurethane copolymer) and Sancure 2060° (INCI name: polyester-polyurethane copolymer) by the company Goodrich, Impranil 85® (INCI name: Water and Polyurethane/Polyester) by the company Bayer and Aquamere H-1511® (INCI name: PVP/polycarbamyl/polyglycol Ester) by the company Hydromer.

Further examples of latex polymers useful in the present invention include (meth)acrylate copolymers such as, for example, acrylate copolymers (acrylates/ethylhexyl acrylate copolymer, sold by Daito Kasei under the tradename Daitosol 5000SJ), butyl acrylate/hydroxypropyl dimethicone acrylate copolymers (Granacrysil BAS by Grant Industries, Inc.), acrylates/C12-C22 alkylmethacrylate copolymers (Allianz OPT by ISP), isododecane and acrylates copolymers (Giovarez AC-5099M by Phoenix), and acrylates/octylacrylamide copolymers (Dermacryl-79 by National Starch & Chemical Company). Particularly useful in the present invention is styrene/acrylates/ammonium methacrylate copolymer (SYNTRAN PC5620 CG, sold by Interpolymer), ammonium acrylates copolymer (VINYSOL 1086WP by Daito Chemical), and STYRENE/ACRYLATES COPOLYMER (Joncryl by BASF) or their mixtures.

Still further examples of suitable latexes include those disclosed in U.S. Pat. Nos. 7,445,770 and/or 7,452,770, the entire contents of both of which are hereby incorporated by reference. For example, suitable latexes include aqueous polyurethane dispersions including the reaction products of:
A) a prepolymer according to the formula:

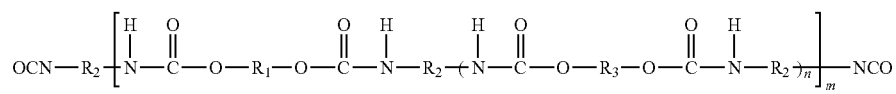

wherein $R_1$ represents a bivalent radical of a dihydroxyl functional compound, $R_2$ represents a hydrocarbon radical of an aliphatic or cycloaliphatic polyisocyanate, $R_3$ represents a radical of a low molecular weight diol, optionally substituted with ionic groups, n is from 0 to 5, and m is >1;
B) at least one chain extender according to the formula:
$H_2N-R_4-NH_2$ wherein $R_4$ represents an alkylene or alkylene oxide radical not substituted with ionic or potentially ionic groups; and
C) at least one chain extender according to the formula:
$H_2N-R_5-NH_2$ wherein $R_5$ represents an alkylene radical substituted with ionic or potentially ionic groups.

Suitable dihydroxyl compounds for providing the bivalent radical $R_1$ include those having two hydroxy groups and having number average molecular weights of from about 700 to about 16,000, and preferably from about 750 to about 5000. Examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. The polyester polyols, polyether polyols and polyhydroxy polycarbonates are preferred. Mixtures of various such compounds are also within the scope of the present invention.

Suitable polyisocyanates for providing the hydrocarbon radical $R_2$ include organic diisocyanates having a molecular weight of from about 112 to 1,000, and preferably from about 140 to 400. Preferred diisocyanates are those represented by the general formula $R_2(NCO)_2$ indicated above in which $R_2$ represents a divalent aliphatic hydrocarbon group having from 4 to 18 carbon atoms, a divalent cycloaliphatic hydrocarbon group having from 5 to 15 carbon atoms, a divalent araliphatic hydrocarbon group having from 7 to 15 carbon atoms or a divalent aromatic hydrocarbon group having 6-15 carbon atoms. Examples of the organic diisocyanates which are suitable include tetramethylene diisocyanate, 1,6-hexamethylene diisocyanate, dodecamethylene diisocyanate, cyclohexane-1,3- and -1,4-diisocyanate, 1-isocyanato-3-isocyanatomethyl-3,5,5-trimethylcyclohexane (isophorone diisocyanate or IPDI), bis-(4-isocyanatocyclohexyl)-methane, 1,3- and 1,4-bis(isocyanatomethyl)-cyclohexane, bis-(4-isocyanato-3-methyl-cyclohexyl)-methane, isomers of toluene diisocyanate (TDI) such as 2,4-diisocyanatotoluene, 2,6-diisocyanatotoluene, mixtures of these isomers, hydrogenated TDI, 4,4'-diisocyanato diphenyl methane and its isomeric mixtures with 2,4'- and optionally 2,2'-diisocyanato diphenylmethane, and 1,5-diisocyanato naphthalene. Mixtures of diisocyanates can, of course, be used. Preferred diisocyanates are aliphatic and cycloaliphatic diisocyanates. Particularly preferred are 1,6-hexamethylene diisocyanate and isophorone diisocyanate.

"Low molecular weight diols" in the context of $R_3$ means diols having a molecular weight from about 62 to 700, preferably 62 to 200. They may contain aliphatic, alicyclic or aromatic groups. Preferred compounds contain only aliphatic groups. The low molecular weight diols having up to about 20 carbon atoms per molecule include ethylene glycol, diethylene glycol, propane 1,2-diol, propane 1,3-diol, butane 1,4-diol, butylene 1,3-glycol, neopentyl glycol, butyl ethyl propane diol, cyclohexane diol, 1,4-cyclohexane dimethanol, hexane 1,6-diol, bisphenol A (2,2-bis(4-hydroxyphenyl) propane), hydrogenated bisphenol A (2,2-bis(4-hydroxycyclohexyl)propane), and mixtures thereof. Optionally, the low molecular weight diols may contain ionic or potentially ionic groups. Suitable lower molecular weight diols containing ionic or potentially ionic groups are those disclosed in U.S. Pat. No. 3,412,054, the contents of which is hereby incorporated by reference. Preferred compounds include dimethylol butanoic acid (DMBA), dimethylol propionic acid (DMBA) and carboxyl-containing caprolactone polyester diol. If lower molecular weight diols containing ionic or potentially ionic groups are used, they are preferably used in an amount such that <0.30 meq of COOH per gram of polyurethane in the polyurethane dispersion are present.

The prepolymer is chain extended using two classes of chain extenders. First, compounds having the formula: $H_2N-R_4-NH_2$ wherein $R_4$ represents an alkylene or alkylene oxide radical not substituted with ionic or potentially ionic groups. Alkylene diamines include hydrazine, ethylenediamine, propylenediamine, 1,4-butylenediamine and piperazine. The alkylene oxide diamines include 3-{2-[2-(3-aminopropoxy)ethoxy]ethoxy}propylamine (also known as dipropylamine diethyleneglycol or DPA-DEG available from Tomah Products, Milton, Wis.), 2-methyl-1,5-pentanediamine (Dytec A from DuPont), hexane diamine, isophorone diamine, and 4,4-methylenedi-(cyclohexylamine), and the DPA-series ether amines available from Tomah Products, Milton, Wis., including dipropylamine propyleneglycol, dipropylamine dipropyleneglycol, dipropylamine tripropyleneglycol, dipropylamine poly(propylene glycol), dipropylamine ethyleneglycol, dipropylamine poly(ethylene glycol), dipropylamine 1,3-propane diol, dipropylamine 2-methyl-1,3-propane diol, dipropylamine 1,4-butane diol, dipropylamine 1,3-butane diol, dipropylamine 1,6-hexane diol and dipropylamine cyclohexane-1,4-dimethanol. Mixtures of the listed diamines may also be used.

The second class of chain extenders are compounds having the formula: $H_2N-R_5-NH_2$ wherein $R_5$ represents an alkylene radical substituted with ionic or potentially ionic groups. Such compounds have an ionic or potentially ionic group and two groups that are reactive with isocyanate groups. Such compounds contain two isocyanate-reactive groups and an ionic group or group capable of forming an ionic group. The ionic group or potentially ionic group can be selected from the group consisting of ternary or quaternary ammonium groups, groups convertible into such a group, a carboxyl group, a carboxylate group, a sulfonic acid group and a sulfonate group. The at least partial conversion of the groups convertible into salt groups of the type mentioned may take place before or during the mixing with water. Specific compounds include diaminosulfonates, such as for example the sodium salt of N-(2-aminoethyl)-2-aminoethane sulfonic acid (AAS) or the sodium salt of N-(2-aminoethyl)-2-aminopropionic acid.

Commercially available examples of such latexes include, but are not limited to, aqueous polyurethane dispersions comprising a reaction product of a prepolymer comprising a dihydroxyl compound, a polyisocyanate, and a low molecular weight diol and at least two diamine compounds and wherein the composition is substantially free of triethanolamine stearate such as, for example, those sold under the BAYCUSAN® name by Bayer such as, for example, BAYCUSAN® C1000 (polyurethane-34), BAYCUSAN® C1001 (polyurethane-34), BAYCUSAN® C1003 (polyurethane-32), and BAYCUSAN® C1004 (polyurethane-35).

Finally, suitable examples of latexes/pseudolatexes can be found, for example, in U.S. Patent application Ser. Nos. 61/541,173, 61/542,131, and 61/542,136, U.S. patent application publication no. 2008/0081054, and U.S. Pat. Nos. 5,538,717, 5,672,647, 6,297,950 and 6,372,201, the entire contents of all of which are hereby incorporated by reference.

Preferably, the latex or pseudolatex is present in the inventive basecoat composition in amounts of the latex and/or pseudolatex dispersion generally ranging from about 5% to about 100% by weight, more preferably from about 10% to about 90%, and more preferably from about 20% to about 80%, by weight, based on the total weight of the composition, including all ranges and subranges in between.

Plasticizers and Coalescents (Optional)

According to particularly preferred embodiments of the present application, the basecoat compositions further comprising at least one plasticizer and/or coalescent are provided. Plasticizers are additives used to optimize the mechanical properties of the films. They tend to reduce the Glass Transition Temperature (Tg) and increase the softness and flexibility of the films. Coalescents are additives used to aid the coalescence of the latex particles, and hence assisting the film formation process.

Preferably, the plasticizer has a distribution coefficient D of less than or equal to 0.1. The distribution coefficient can be determined in accordance with the teaching of "A method to predict the distribution coefficient of coalescing agents between latex particles and the water phase," *Progress in Organic Coatings*, vol. 30, 1997, pp. 173-177, the disclosure of which is specifically incorporated by reference herein.

Preferably, the plasticizer has a boiling point measured at ambient pressure of less than or equal to 285° C., preferably less than or equal to 270° C., and preferably less than or equal to 250° C. In the present specification, the boiling point values are to be considered accurate to ±2° C. owing to the uncertainties of boiling point measurement.

Any plasticizing agent typically found in nail polish compositions can be used. Examples of suitable plasticizers include, but are not limited to, glycols and their ester derivatives, esters of acids, in particular carboxylic acids, such as citrates, adipates, carbonates, tartrates, phosphates or sebacates, oxyethylenated derivatives, such as oxyethylenated oils, and their mixtures. For example, suitable plasticizing agents include, but are not limited to, diisobutyl adipate, the ester of teributyl acid and 2,2,4-trimethylpentane-1,3-diol, diethyl adipate, diethyl phthalate, dibutyl phthalate, dioctyl phthalate, butyl 2-ethylhexyl phthalate, dimethyl sebacate, dibutyl sebacate, ethyl stearate, 2-ethylhexyl palmitate, dipropylene glycol n-butyl ether, tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl) acetylcitrate, dibutyl tartrate, camphor, and mixtures thereof.

In accordance with preferred embodiments, the plasticizer, if present, is preferably present in the basecoat composition in an amount from about 0.1% to about 25% by weight, preferably from about 0.5% to about 20% by weight, preferably from about 1% to about 10% by weight, of the total weight of the composition, including all ranges and subranges there between.

According to particularly preferred embodiments of the present application, basecoat compositions further comprising at least one coalescent agent are provided. The coalescent agent promotes the coalescence of the polymer(s) in the composition.

Preferably, the coalescent agent has a distribution coefficient D' of greater than or equal to 0.5, measured in accordance with the above-referenced "A method to predict the distribution coefficient of coalescing agents between latex particles and the water phase," *Progress in Organic Coatings*, vol. 30, 1997, pp. 173-177.

Preferably, the coalescent agent has a boiling point measured at ambient pressure ranging from 90° C. to 180° C., preferably from 150° C. to 180° C.

Any coalescent agent typically found in nail polish compositions can be used. Examples of suitable plasticizers include, but are not limited to, propylene glycol n-butyl ether, propylene glycol butyl ether, dipropylene glycol dimethyl ether, propylene glycol methyl ether acetate, propylene glycol propyl ether, dipropylene glycol dibenzoate, methyl lactate, ethyl lactate, isopropyl lactate, and mixtures thereof.

In accordance with preferred embodiments, the coalescent agent, if present, is preferably present in the basecoat composition in an amount from about 0.1% to about 25% by weight, preferably from about 1% to about 15% by weight, preferably from about 3 to about 10% by weight, of the total weight of the basecoat composition, including all ranges and subranges therebetween.

Abrasive Agents/Fillers (Optional)

The basecoat compositions according to the invention may further comprise one or a plurality of abrasive agents.

The term "abrasive agents" should be understood to refer to inorganic or synthetic colorless or white particles of any shape, insoluble in the medium of the composition regardless of the temperature at which the composition is manufactured. The abrasive agents may particularly be used to modify the rheology or texture of the composition.

In this particular invention, it has been found that abrasive agents increase adhesion between the basecoat and the second coat (color coat) of the nail system. It is believed that the increased adhesion between the basecoat and the second coat (color coat) due to the presence of said abrasive agents allows for easier peel removal of the nail treatment application (peel off in one piece) without leaving any remaining film on the nail plate.

The abrasive agents may be mineral or organic particles of any shape, in sheet, spherical or oblong form, regardless of the crystallographic shape (for example sheet, cubic, hexagonal, orthorhombic, etc). Mention may be made of talc, mica, silica, kaolin, polyamide (Nylon™) (Orgasol® from Atochem), poly-β-alanine and polyethylene powders, tetrafluoroethylene polymer powders (Teflon®), lauroyllysine, starch, boron nitride, polymeric hollow microspheres such as those of polyvinylidene chloride/acrylonitrile like Expancel® (Nobel Industrie), acrylic acid copolymers (Polytrap® from Dow Corning) and silicone resin microbeads (Tospearls® from Toshiba, for example), elastomer polyorganosiloxane particles, precipitated calcium carbonate, magnesium carbonate and hydro-carbonate, hydroxyapatite, hollow silica microspheres (Silica Beads® from Maprecos), glass or ceramic microcapsules, metallic soaps derived from carboxylic organic acids having 8 to 22 carbon atoms, preferably from 12 to 18 carbon atoms, for example zinc, magnesium or lithium stearate, zinc laurate, magnesium myristate. One of the preferred abrasive agents used in this invention are precipitated silicas having wax treated surface, such as Silica (and) Polyethylene (ACEMATT OK 412® from Evonic). Another useful abrasive agents belong to the group of synthetically silicated clays, such as Lithium Magnesium Sodium Silicate (LAPONITE XLG® from BYK Additives & Instruments).

In this particular invention, abrasive agents can be present particularly at a content ranging from about 0.01% to about 10% by weight, preferably ranging from about 0.1% to about 5% by weight, most preferably from about 0.5% to about 1.5%, in relation to the total weight of the basecoat composition.

Second Coat (Sometimes Referred to as "Color Coat") and Topcoat (Optional)

According to the present invention, the nail composition system includes a second coat (preferably a color coat) for application to nails. The second coat of this composition is a UV curable, photocrosslinkable cosmetic composition.

More particularly, the present invention relates to a photocrosslinkable composition, equally suitable for use as a colored nail varnish and as well as a transparent finishing composition (topcoat).

The present invention also relates to a nail treatment system containing a photocrosslinkable cosmetic composition (second coat), comprising: at least one photocrosslinkable urethane (meth)acrylate compound P1 comprising at least one structural unit:

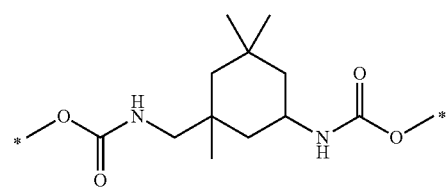

at least one methacrylate monomer;
at least one photoinitiator;
optionally at least one photocrosslinkable urethane (meth) acrylate compound P2;
optionally at least one film-forming polymer P3;
optionally at least one pigment; and
(optionally at least one organic solvent.

Photocrosslinkable Urethane (Meth)Acrylate Compound ("P1")

The term "urethane (meth)acrylate compound" refers to any compound comprising at least one urethane function —O—C(O)—NH—, also known as a carbamate, and at least one (meth)acrylate function according to the formula

H₂C=C(R)—C(O)—O— where R=H or CH₃.

The "urethane" function is also referred to as a "carbamate" function.

The urethane (meth)acrylate compound may be chosen from the group consisting of urethane poly(meth)acrylate compounds, particularly in the group consisting of urethane di(meth)acrylate compounds, and more particularly in the group consisting of urethane dimethacrylate compounds.

According to the present invention, the term "poly(meth)acrylate compound" refers to a (meth)acrylate compound comprising a plurality of (meth)acrylate functions.

In this way, the term "poly(meth)acrylate compound" may refer to a compound comprising at least two methacrylate functions, or at least two acrylate functions, or at least one methacrylate function and at least one acrylate function.

As urethane (meth)acrylate compounds, particular mention may be made of urethane dimethacrylate compounds.

The term "urethane dimethacrylate compound" refers to any compound comprising at least one urethane function —O—C(O)—NH—, and two methacrylate functions according to the formula

H₂C=C(CH₃)—C(O)—O—.

The second coat composition according to the invention comprises at least one first photocrosslinkable compound, referred to as P1, which is a urethane (meth)acrylate compound and which comprises at least one structural unit:

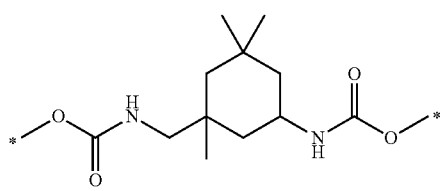

The photocrosslinkable compound P1 is preferably of formula:

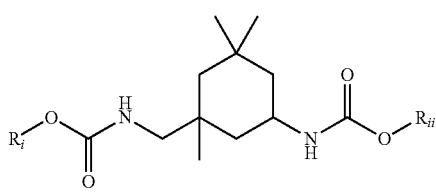

where $R_i$ and $R_{ii}$ are identical or different groups, each representing a $C_1$-$C_6$ alkyl group substituted with one or a plurality of (meth)acrylate groups, or a polyurethane group, comprising 2 to 20 urethane units, said polyurethane being substituted by one or a plurality of (meth)acrylate groups.

The term "polyurethane group" refers to a group obtained from polymerizing a mixture of monomers comprising isocyanate functions and monomers comprising alcohol functions.

According to one embodiment, the photocrosslinkable compound P1 is of formula (I):

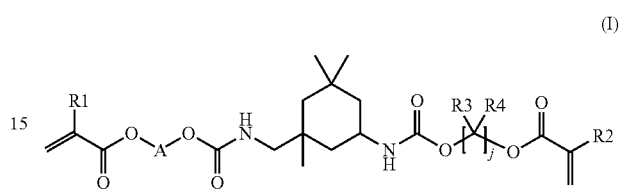

wherein:
j is an integer ranging from 1 to 10, preferably equal to 2,
R1 and R2, identical or different, represent a hydrogen atom or a methyl group,
R3 and R4, identical or different, represent a hydrogen atom or a $C_1$-$C_{10}$ alkyl chain, preferably a hydrogen atom or a methyl group, and
-A- represents a linear or branched $C_1$-$C_{10}$ divalent alkylene group, or a divalent polyurethane group, comprising from 2 to 20 urethane units.

Preferably, R1 and R2 are methyl groups

According to another embodiment, the photocrosslinkable compound P1 is of formula (II):

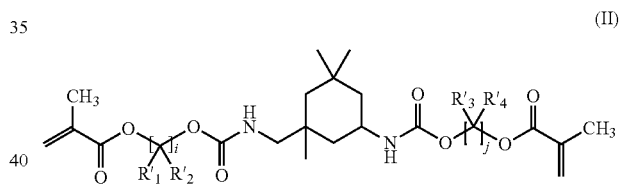

wherein:
i is an integer ranging from 1 to 6, preferably equal to 2,
j is an integer ranging from 1 to 6, preferably equal to i, and preferentially equal to 2, and
$R'_1$, $R'_2$, $R'_3$, and $R'_4$, identical or different, represent a hydrogen atom or a $C_1$-$C_{10}$ alkyl chain, preferably a hydrogen atom or a methyl group.

The composition according to the invention optionally comprises a mixture of different compounds P1.

The at least one photocrosslinkable urethane (meth)acrylate compound P1 is preferably present at a total content greater than or equal to 1% by weight, in relation to the total weight of the photocrosslinkable composition of second coat or topcoat, advantageously ranging from about 1% to about 80%, preferably from about 5% to about 75%, more preferably from about 10% to about 70%, advantageously from about 25% to about 65% by weight in relation to the total weight of the photocrosslinkable composition.

As an example of a suitable photocrosslinkable compound P1, mention may be made of Isophorone Urethane Dimethacrylate (X-851-1066 available from ESSTECH, Inc.).

(Meth)Acrylate Monomer (Ethylenically Unsaturated Monomer)

(Meth)acrylate monomer refers to a compound comprising a single (meth)acrylate function according to the formula $H_2C=C(R)-C(O)-O-$, where R=H or $CH_3$ capable of reacting with other molecules. In various embodiments, the at least one (meth)acrylate monomer may have a molecular weight ranging from 100 to about 300, for example, from about 120 to about 200.

In various embodiments, the at least one (meth)acrylate monomer may be chosen from compounds of general formula (I):

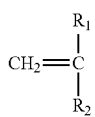

(I)

wherein:
- $R_1$ is chosen from hydrogen and $C_1$-$C_{30}$ alkyl radicals and $R_2$ is chosen from —COOM radicals, wherein M is chosen from $C_1$-$C_{30}$ straight or branched chain alkyl radicals optionally substituted with at least one hydroxyl group or heterocycle, and from polyalkyleneoxy groups comprising preferably from 2 to 4 units, and from aromatic, alicyclic, and bicyclic rings optionally substituted with at least one substituent chosen from $C_1$-$C_{30}$ straight or branched chain alkyl radicals which may be substituted with at least one hydroxyl group. In another embodiment, the at least one (meth)acrylate monomer may be chosen from monomers of formula (I), wherein $R_1$ is chosen from hydrogen and $CH_3$, and
- $R_2$ is chosen from —COOM radicals, wherein M is chosen from $C_1$-$C_{10}$ straight or branched chain alkyl radicals optionally substituted with at least one hydroxyl group or heterocycle, and from aromatic, alicyclic, and bicyclic rings optionally substituted with at least one substituent chosen from $C_1$-$C_{30}$ straight or branched chain alkyl radicals which may be substituted with at least one hydroxyl group.

For example, the (meth)acrylate monomer may be chosen from (meth)acrylate monomers, such as methyl (meth)acrylate (MMA), ethyl (meth)acrylate (EMA), butyl (meth)acrylate (BMA), and polyethylene monomethacrylate such as diethylene glycol monomethacrylate, polypropylene glycol monomethacrylate such as dipropylene glycol monomethacrylate, and isobornyl (meth)acrylate, and tetrahydrofurfuryl (meth)acrylate (THFMA), and hydroxyalkyl (meth)acrylate monomers, such as hydroxypropyl methacrylate (HPMA), hydroxyethyl (meth)acrylate (HEMA), and butoxyethyl (meth)acrylate (BEMA).

Particularly useful for this invention is tetrahydrofurfuryl methacrylate (THFMA) available from Esstech, Inc. (X-958-7466).

In an embodiment, the (meth)acrylate monomer is present in the composition of the invention in the amount from about 0.01% to about 50% by weight, typically from about 5% to about 30% by weight, more particularly from about 10% to about 25% by weight, including all ranges and subranges there between, all weights being based on the total weight of the photocrosslinkable composition of the second coat or topcoat.

Photoinitiator

The second and optionally the top compositions according to the invention comprise at least one photoinitiator.

The photoinitiators suitable for use according to the present invention are known in the art and are described, for example in "Les photoinitiateurs dans la réticulation des revêtements", G. Li Bassi, Double Liaison-Chimie des Peintures, No. 361, November 1985, p.34-41; "Applications industrielles de la polymérisation photoinduite", Henri Strub, L'Actualité Chimique, February 2000, p.5-13; and "Photopolymères: considérations théoriques et réaction de prise", Marc, J. M. Abadie, Double Liaison-Chimie des Peintures, No. 435-436, 1992, p.28-34.

These photoinitiators include:
- α-hydroxyketones, marketed for example under the names DAROCUR® 1173 and 4265, IRGACURE® 184, 2959, and 500 by BASF, and ADDITOL® CPK by CYTEC,
- α-aminoketones, marketed for example under the names IRGACURE® 907 and 369 by BASF,
- aromatic ketones marketed for example under the name ESACURE® TZT by LAMBERTI. Mention may also be made of thioxanthones marketed for example under the name ESACURE® ITX by LAMBERTI, and quinones. These aromatic ketones generally require the presence of a hydrogen donor compound such as tertiary amines and particularly alkanolamines. Mention may particularly be made by the tertiary amine ESACURE® EDB marketed by LAMBERTI.
- α-dicarbonyl derivatives of which the most common is benzyl dimethyl ketal marketed under the name IRGACURE® 651 by BASF. Further commercial products are marketed by LAMBERTI under the name ESACURE® KB1, and acylphosphine oxides, such as for example bis-acylphosphine oxides (BAPO) marketed for example under the names IRGACURE® 819, 1700, and 1800, DAROCUR® 4265, LUCIRIN® TPO, and LUCIRIN® TPO-L by BASF.

Preferably, the photoinitiator of the composition according to the invention is chosen from the group consisting of α-hydroxyketones, α-aminoketones, aromatic ketones preferably associated with a hydrogen donor compound, aromatic α-diketones, acylphosphine oxides, and mixtures thereof.

Preferably, the photoinitiator of the composition according to the invention is an α-hydroxyketone, such as for example IRGACURE® 184 (BASF), an acylphosphine oxide, such as for example LUCIRIN® TPO-L (BASF), or mixtures thereof.

A mixture of photoinitiators absorbing light radiation at various wavelengths may also be used in the photocrosslinkable composition according to the invention. The absorption spectrum of the photocrosslinkable composition can thus be adapted to the emission spectrum of the light sources used.

Preferably, the composition according to the invention comprises a mixture of two different photoinitiators, such as for example a mixture of an α-hydroxyketone and an acylphosphine oxide.

A particular group of photoinitiators suitable for use in the photocrosslinkable cosmetic compositions according to the present invention is that of copolymerizable photoinitiators. It consists of molecules comprising both a photoinitiator group capable of photoinduced radical splitting and at least one double ethylene bond. The photoinitiators in this group offer the advantage, in relation to the conventional photoinitiators listed above, of being suitable for being incorporated, via the double bond, into the macromolecular system. This possibility reduces the content of free residual photoinitiators not having undergone photoinduced radical splitting and thus enhances the safety of the layer C1.

As examples of such copolymerizable photoinitiators, mention may be made of benzophenone acrylate derivatives marketed by CYTEC under the names EBECRYL® P36, EBECRYL® P37.

In one preferred embodiment of the invention, polymer photoinitiators or photoinitiators bound onto a high molar mass molecule are used. The choice of such a high mass photoinitiator offers the same advantage as selecting only polymeric copolymerizable compounds, i.e. enhanced safety of the photocrosslinkable cosmetic compositions due to the absence of very reactive molecules liable to diffuse to neighboring biological substrates. The mean molar mass by weight of the photoinitiator is preferably at least equal to 500 g/mol.

For example, mention may be made of an α-hydroxyketone oligomer corresponding to the following formula:

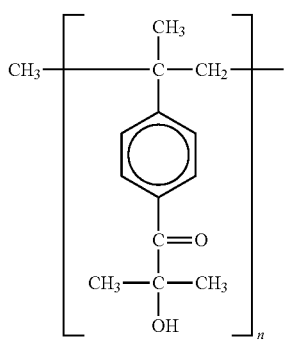

n=2 or 3 and which is marketed under the name ESACURE® KIP 150 by LAMBERTI.

The polymer on which the photoinitiator group is bound may optionally comprise one or a plurality of double ethylene bonds for optionally incorporating, into the macromolecular network, photoinitiator molecules not having undergone photoinduced splitting.

As examples of such high molar mass photoinitiators bearing double ethylene bonds, mention may be made of those corresponding to the following formulae:

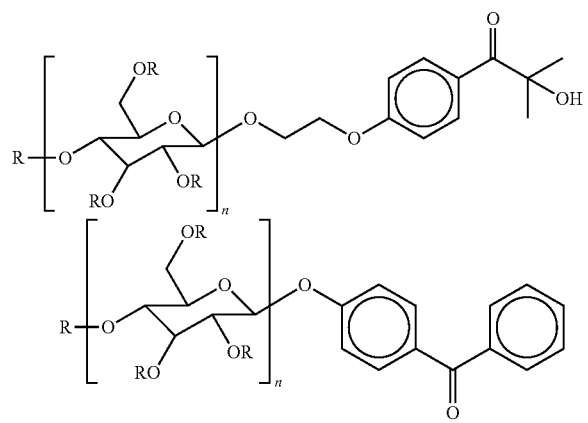

with n=1 to 20
R=H or

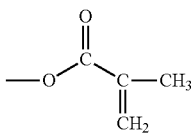

or

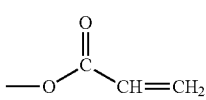

These structures are described in the following articles: S. Knaus, *Pure Appl. Chem.*, A33(7), 869 (1996); S. Knaus, *J. Polym. Sci, Part A=Polym. Chem.*, 33, 929 (1995); and R. Liska, *Rad'Tech Europe* 97, Lyon, F, 1997, Conference Proceedings.

The content of the photoinitiator(s) used is dependent on a large number of factors such as the reactivity of the various constituents of the mixture, the presence of pigments or dyes, the crosslinking density sought, the intensity of the light source or the exposure time.

In order to obtain satisfactory mechanical properties of the inventive compostions, the at least one photoinitiator is preferably present in a total content greater than or equal to 0.1%, preferably ranging from about 1% to about 10%, preferentially ranging from about 2% to about 7% by weight in relation to the total weight of the photocrosslinkable composition of the second coat or topcoat.

Photocrosslinkable Compound ("P2") (Optional)

The second, and when used the top coat compositions according to the invention comprise at least one second photocrosslinkable compound, referred to as P2, which is a urethane (meth)acrylate compound and which optionally may further comprise at least one polyethylene glycol chain.

The term "polyethylene glycol chain" refers to a divalent radical according to formula $-[C_2H_4O]_m-$, wherein m is an integer ranging from 2 to 100, preferably from 5 to 50

According to one embodiment, the photocrosslinkable compound P2 is of formula (III):

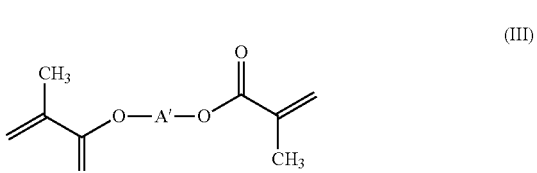

(III)

wherein -A'- represents a $C_1$-$C_{100}$ divalent hydrocarbon radical, optionally substituted with alkyl groups, said radical being interspersed with at least one urethane function —O—C(O)—NH—, at least one polyethylene glycol chain as defined above, and optionally with heteroatoms, such as oxygen, nitrogen, sulfur atoms, or saturated, aromatic or heteroaromatic cyclic divalent groups, such as cycloalkylene, arylene or heteroarylene groups.

Within the scope of the present invention, the heteroatoms include oxygen, nitrogen and sulfur atoms.

According to the present invention, the "alkyl" groups represent straight or branched chain saturated hydrocarbon radicals, comprising from 1 to 10 carbon atoms, preferably from 1 to 6 carbon atoms. Mention may particularly be made, when they are linear, of methyl, ethyl, propyl, butyl, pentyl, hexyl, octyl, nonyl and decyl radicals. Mention may particularly be made, when they are branched or substituted with one or a plurality of alkyl radicals, of isopropyl, tert-butyl, 2-ethylhexyl, 2-methylbutyl, 2-methylpentyl, 1-methylpentyl and 3-methylheptyl radicals.

The "cycloalkene" radical is a non-aromatic saturated or partially unsaturated mono-, bi- or tri-cyclic divalent hydrocarbon radical, comprising from 3 to 20 carbon atoms, and preferably from 3 to 10 carbon atoms, such as in particular cyclopropylene, cyclopentylene, cyclohexylene or adamantylene, optionally substituted with alkyl groups, and the corresponding rings containing one or a plurality of unsaturations.

In this way, within the scope of the present invention, the term "cycloalkylene" also covers "heterocycloalkylene" radicals denoting non-aromatic saturated or partially unsaturated mono- or bicyclic divalent radicals, of 3 to 8 carbon atoms, comprising one or a plurality of heteroatoms chosen from N, O or S.

The term "arylene" refers to a mono or bicyclic aromatic divalent hydrocarbon radical, comprising from 6 to 30, preferably from 6 to 10, carbon atoms. Of the arylene radicals, mention may particularly be made of the phenylene or naphthylene radical, more particularly substituted with at least one halogen atom. If the arylene radical comprises at least one heteroatom, the term "heteroarylene" radical is used. In this way, the term "heteroarylene" refers to an aromatic divalent radical comprising one or a plurality of heteroatoms chosen from nitrogen, oxygen or sulfur, comprising from 5 to 30, and preferably from 5 to 10, carbon atoms. Of the heteroarylene radicals, mention may be made of pyrazinylene, thienylene, oxazolylene, furazanylene, pyrrolylene, 1,2,4-thiadiazolylene, naphthyridinylene, pyridazinylene, quinoxalinylene, phtalazinylene, imidazo[1,2-a]pyridinene, imidazo[2,1-b]thiazolylene, cinnolinylene, triazinylene, benzofurazanylene, azaindolylene, benzimidazolylene, benzothienylene, thienopyridylene, thienopyrimidinylene, pyrrolopyridylene, imidazopyridylene, benzoazaindolene, 1,2,4-triazinylene, benzothiazolylene, furanylene, imidazolylene, indolylene, triazolylene, tetrazolylene, indolizinylene, isoxazolylene, isoquinolinylene, isothiazolylene, oxadiazolylene, pyrazinylene, pyridazinylene, pyrazolylene, pyridylene, pyrimidinylene, purinylene, quinazolinylene, quinolinylene, isoquinolylene, 1,3,4-thiadiazolylene, thiazolylene, triazinylene, isothiazolylene, carbazolylene, along with the corresponding groups obtained from the fusion thereof or fusion with the phenyl nucleus.

According to another embodiment, the photocrosslinkable compound P2 is of formula (IV):

wherein:
i is an integer ranging from 1 to 6, preferably equal to 2,
j is an integer ranging from 1 to 6, preferably equal to i, and preferentially equal to 2,
k is an integer ranging from 2 to 100, preferably from 5 to 50,
l is an integer ranging from 1 to 10,
R1, R3, R3 and R4, identical or different, represent a hydrogen atom or a $C_1$-$C_{10}$ alkyl chain, preferably a hydrogen atom or a methyl group,
-A"- represents a linear or branched $C_1$-$C_{20}$ divalent hydrocarbon alkylene group, or a $C_5$-$C_{20}$ divalent cycloalkylene radical.

Preferably, -A"- represents a radical according to the formula:

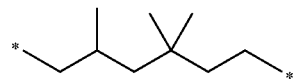

A photocrosslinkable compound P2 suitable for the implementation of the invention is for example PEG 400 Extended Urethane Dimethacrylate (X-726-0000 from ESSTECH, Inc.).

The composition according to the invention optionally comprises a mixture of different compounds P2.

The compound(s) P2 is (are) preferably present at a total content greater than or equal to 1% by weight, in relation to the total weight of the photocrosslinkable composition of the second coat or topcoat, advantageously ranging from about 1 to about 80%, preferably from about 20 to about 70%, more preferably from about 40% to about 65%, preferentially from about 45% to about 60% by weight in relation to the total weight of the photocrosslinkable composition.

Film-Forming Polymer ("P3") (Optional)

The second, and when used the topcoat, compositions according to the invention preferably comprise at least one film-forming polymer P3, different to the photocrosslinkable compound P1 and different to the photocrosslinkable compound P2.

This film-forming polymer may be chosen from the group consisting of radical or polycondensate type synthetic polymers, polymers of natural origin, and mixtures thereof.

A film-forming polymer suitable for the invention may be chosen from polysaccharide derivatives, such as cellulose or guar gum derivatives. One preferential polysaccharide derivative suitable for the invention may be nitrocellulose or a polysaccharide ester or alkylether.

The term "polysaccharide ester or alkylether" refers to a polysaccharide consisting of repeat units comprising at least two identical or different rings and having a degree of substitution per saccharide unit between 1.9 and 3, preferably between 2.2 and 2.9, and more particularly between 2.4 and 2.8. The term substitution refers to the functionalization (IV)

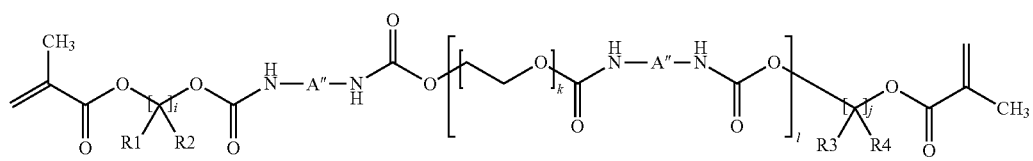

of hydroxyl groups into ester and/or alkylether functions, and/or the functionalization of carboxyl groups into ester functions.

In other words, it may consist of a polysaccharide, partially or totally substituted with ester and/or alkylether groups. Preferably, the hydroxyl groups may be substituted with $C_2$-$C_4$ ester and/or alkylether functions.

Particular mention may be made of cellulose esters (such as cellulose acetobutyrates or cellulose acetopropionates), cellulose alkylethers (such as ethylcelluloses), and ethylguars.

A film-forming polymer suitable for the invention may be chosen from synthetic polymers such as polyurethanes, acrylic polymers, vinyl polymers, polyvinylbutyrals, alkyd resins and ketone/aldehyde resins, resins from aldehyde condensation products, such as aryl sulfonamide formaldehyde resins such as toluene sulfonamide formaldehyde resin, aryl-sulfonamide epoxy resins or ethyl tosylamide resins.

In particular, it may consist of (meth)acrylate homopolymers and copolymers.

A film-forming polymer suitable for the invention may also be chosen from polymers of natural origin, such as plant resins such as dammars, elemi, copals, benzoin; gums such as shellac, sandarac and mastic.

As a film-forming polymer, the toluene sulfonamide formaldehyde resins "Ketjentflex MS80" from AKZO or "Santolite MHP", "Santolite MS 80" from FACONNIER or "RESIMPOL 80" from PAN AMERICANA, the alkyd resin "BECKOSOL ODE 230-70-E" from DAINIPPON, the acrylic resin "ACRYLOID B66" from ROHM & HAAS, the polyurethane resin "TRIXENE PR 4127" from BAXENDEN, the acetophenone/formaldehyde resin marketed under the reference Synthetic Resin SK by Degussa may notably be used.

According to one preferred particular embodiment, the film-forming polymer P3 is chosen from the group consisting of polysaccharides and polysaccharide derivatives, preferably from nitrocellulose and polysaccharide ethers and esters, particularly $C_2$-$C_4$, and more preferentially from cellulose acetobutyrates, cellulose acetopropionates, ethylcelluloses, ethylguars, and mixtures thereof.

The second coat, and when used the topcoat compositions according to the invention optionally comprise a mixture of different polymers P3.

According to one particularly preferred embodiment, the film-forming polymer P3 is chosen from the group consisting of nitrocellulose, cellulose acetopropionate, cellulose acetobutyrate, and (meth)acrylate homopolymers and copolymers.

Advantageously, the film-forming polymer P3 is a (meth) acrylate homopolymer or copolymer, preferably an acrylate copolymer.

According to this invention the preferred film-forming polymer is chosen from butyl acetate (and) acrylates copolymer (PECOREZ AC 50 by PHOENIX CHEMICAL), cellulose acetate butyrate (CAB-381-0,5 from EASTMAN CHEM.) or their mixtures.

The at least one film-forming polymer(s) P3 is preferably present at a total content greater than or equal to 0.1%, preferably from about 0.2% to about 10%, preferably from about 1% to about 8%, preferentially from about 2% to about 5%, by weight in relation to the total weight of the photocrosslinkable composition of the second coat or topcoat.

Coloring Agent (Optional)

According to one embodiment, the second coat, and optionally also the topcoat according to the invention may further comprise at least one coloring agent chosen from the group consisting of soluble dyes, pigments, nacres and glitter.

The composition according to the invention according to this embodiment is typically used as colored nail varnish.

The term "soluble dyes" should be understood to refer to organic, inorganic or organometallic compounds, soluble in the composition according to the invention and intended to color said composition.

The dyes are, for example, Sudan Red, DC Red 17, DC Green 6, 13-carotene, soybean oil, Sudan brown, DC Yellow 11, DC Violet 2, DC Orange 5 and Quinoline Yellow.

The term "pigments" should be understood to refer to inorganic or organic, white or colored particles of any shape, insoluble in the composition according to the invention and intended to color said composition.

The term "nacres" should be understood to refer to iridescent particles of any shape, particularly produced by some mollusks in their shell or by synthetic means.

The pigments may be white or colored, inorganic and/or organic. Of the inorganic pigments, mention may be made of titanium dioxide, optionally surface-treated, zirconium or cerium oxides, along with zinc, iron (black, yellow or red) or chromium oxides, manganese violet, ultramarine blue, chromium hydrate and iron blue, metallic powders such as aluminum powder, copper powder.

Of the organic pigments, mention may be made of carbon black, D & C type pigments, and lacquers based on cochineal carmine, barium, strontium, calcium, aluminum.

Mention may also be made of effect pigments such as particles comprising a natural or synthetic organic or inorganic substrate, for example glass, acrylic resins, polyester, polyurethane, polyethylene terephthalate, ceramics, aluminas and optionally coated with metallic substances such as aluminum, gold, copper, bronze, or with metal oxides such as titanium dioxide, iron oxide, chromium oxide, inorganic or organic pigments and mixtures thereof.

The pearlescent pigments may be chosen from white pearlescent pigments such as mica coated with titanium, or bismuth oxychloride, colored pearlescent pigments such as titanium mica coated with iron oxides, titanium mica coated with iron blue and chromium oxide in particular, titanium mica coated with an organic pigments of the aforementioned type and pearlescent pigments based on bismuth oxychloride.

Pigments with goniochromatic properties may be used, particularly liquid crystal or multilayer pigments.

Optical brighteners or fibers optionally coated with optical brighteners may also be used.

The at least one coloring agent is present in a total content greater than or equal to 0.1% by weight in relation to the total weight of the layer, ranging preferably from about 0.1 to about 5%, advantageously from about 0.2 to about 3% by weight in relation to the total weight of the second coat or top coat composition.

If either the second coat or the top coat composition comprises pigments and/or dyes, it is particularly advisable to adapt the absorption spectrum of the pigments and/or dyes used to that of the photoinitiators, or conversely the absorption spectrum of the photoinitiators to that of the pigments and/or dyes used, so as to prevent both types of compounds from absorbing light at the same wavelengths. Indeed, the absorption of light by the pigments and/or dyes would render the photoinitiators present beyond a specific depth of the coat almost completely ineffective.

According to a further embodiment, the second coat according to the invention may be free from coloring agents as defined above.

According to a further embodiment the invention comprises a second coat which is colored. This embodiment may further comprise an additional, third coat, sometimes referred to as a "topcoat". The topcoat typically comprises the same components as defined above the second coat.

Preferably, the topcoat is clear and/or transparent. As used herein, the term "transparent" refers to that the composition has a HAZEBYK index of less than 5 as measured with a KYKHAZEGLOSS type gloss meter.

According to a further embodiment, the topcoat composition according to the invention may be any conventional nail cosmetic composition.

Solvents Useful in the Second Coat (Optional)

The second coat, and when used the topcoat compositions according to the present invention generally further comprise at least one solvent chosen from organic and inorganic solvents.

The suitable solvents may particularly be chosen from:
liquid ketones at ambient temperature such as methylethylketone, methylisobutylketone, diisobutylketone, isophorone, cyclohexanone and acetone, liquid alcohols at ambient temperature such as ethanol, isopropanol, diacetone-alcohol, 2-butoxyethanol and cyclohexanol, liquid glycols at ambient temperature such as ethyleneglycol, propyleneglycol, pentyleneglycol and glycerol,
liquid propyleneglycol ethers at ambient temperature such as propyleneglycol monomethylether, propyleneglycol monomethyl ether acetate and dipropyleneglycol mono-n-butylether,
short-chain esters (comprising in total from 3 to 8 carbon atoms) such as ethyl acetate, methyl acetate, propyl acetate, n-propyl acetate, iso-propyl acetate, n-butyl acetate, iso-butyl acetate, ter-butyl acetate and isopentyl acetate,
liquid alkanes at ambient temperature such as decane, heptane, dodecane and cyclohexane,
liquid aromatic hydrocarbons at ambient temperature such as toluene and xylene,
liquid silicones at ambient temperature, and
mixtures thereof.

The second coat, and when used the topcoat compositions according to the invention preferably comprise so-called volatile solvents.

The term "volatile solvent" refers to a solvent capable of evaporating on contact with keratin matter, in less than one hour, at ambient temperature and at atmospheric pressure.

The volatile solvent(s) according to the invention are liquid solvents at ambient temperature, having a vapor pressure different to zero, at ambient temperature and atmospheric pressure, particularly ranging from 0.13 Pa to 40,000 Pa (from $10^{-3}$ to 300 mm Hg), particularly ranging from 1.3 Pa to 13,000 Pa (from 0.01 to 100 mm Hg), and more specifically ranging from 1.3 Pa to 1300 Pa (from 0.01 to 10 mm Hg).

On the other hand, a "non-volatile solvent" evaporates on contact with keratin matter in more than one hour, at ambient temperature and atmospheric pressure.

Preferably, the second and when used the topcoat compositions comprise a solvent chosen from acetone, ethyl acetate, propyl acetate and butyl acetate.

Preferably, the solvent of the compositions according to the invention is butyl acetate.

The total solvent content in photocrosslinkable composition of the second coat or topcoat may range from about 0.5% to about 50% by weight in relation to the total weight of the composition.

According to one embodiment, the solvent content in the photocrosslinkable composition of the second coat or topcoat ranges from about 0.5% to about 10%, preferentially from about 0.7% to about 8%, advantageously from about 1% to about 5% by weight in relation to the total weight of said composition.

Auxiliaries/Additives (Optional)

The basecoat, the second coat (color coat), and the topcoat of the layers of the nail treatment system of the present invention may additionally comprise an additive or auxiliary commonly used in cosmetic compositions and known to a person skilled in the art as being capable of being incorporated into said compositions. Such additives or auxiliaries may be chosen from thickeners, coalescents, preservatives, fragrances, oils, waxes, surfactants, antioxidants, agents for combating free radicals, spreading agents, wetting agents, dispersing agents, antifoaming agents, neutralizing agents, stabilizing agents, active principles chosen from essential oils, UV screening agents, sunscreens, moisturizing agents, vitamins, proteins, ceramides, plant extracts, fibers, and the like, and their mixtures.

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the second coat or top coat composition in a proportion from about 0% to about 99% (such as from about 0.01% to about 90% relative to the total weight of the composition and further such as from about 0.1% to about 50% (if present), including all ranges and subranges therebetween.

Needless to say, the composition of the invention should be cosmetically or dermatologically acceptable, i.e., it should contain a non-toxic physiologically acceptable. The composition may be in any galenic form normally employed in the cosmetic and dermatological fields which is suitable for topical administration onto nails.

According to preferred embodiments of the present invention, methods of making up or protecting nails comprising applying to the nails at least one basecoat, at least one second coat (color coat), and optionally, at least one topcoat to nails in an amount sufficient to makeup or protect the nails are provided.

According to preferred embodiments, at least one basecoat and at least one second coat (color coat) are further applied to the nails in the following order: nail/basecoat/second coat (color coat)/topcoat (optional).

According to preferred embodiments, at least one basecoat and at least one second coat (color coat) are further applied to the nails in the following order: nail/basecoat/second coat (color coat)/color coat/topcoat (optional).

According to preferred embodiments, at least one basecoat and at least one second coat (color coat) are further applied to the nails in the following order: nail/basecoat/second coat (color coat)/second coat (color coat)/topcoat.

According to preferred embodiments of the present invention, methods for making up and/or protecting nails comprising applying to the nails at least one basecoat and at least one second coat (color coat), wherein the basecoat comprises water and at least one non-UV curable adhesive latex or pseudolatex, in an amount sufficient to makeup or protect the nails are provided. The basecoat preferably further comprises at least one water-soluble film forming agent and/or at least one plasticizer and/or at least one coalescent agent. According to preferred embodiments, the basecoat further contains at least one abrasive agent.

"Making up" as used herein means to provide decoration (for example, color) to the nail. "Protecting" as used herein means to inhibit damage to the nail (for example, chipping) by providing a protective layer on the nail.

EXAMPLES

The following Examples are intended to be non-restrictive and explanatory only, with the scope of the invention being defined by the claims.

Method of Preparation of Inventive Compositions
Water-Based Base Coat:
1. The water phase was prepared by dissolving Lithium Magnesium Sodium in water, and then the non-UV curable film formers (latexes) were added and mixed until homogenous mixture was obtained.
2. The oil phase was prepared by combining and mixing the remaining ingredients with exception to silica.
3. The oil phase was combined with the aqueous phase and mixed well.
4. Silica was then added and mixing continued until the composition had uniform structure.

UV Gel Color Coat:
1. Stearalkonium Hectorite was combined with 10% of Tetrahydrofurfuryl Methacrylate and mixed with a Rayneri laboratory mixer until a homogeneous blend was obtained.
2. The pigments were ground in the mixture of Isophorone Urethane Dimethacrylate and Tetrahydrofurfuryl Methacrylate premixed at the ratio of 60:40, using a triple roller.
3. Then the mixture of Cellulose Acetate Butyrate and the remaining Tetrahydrofurfuryl methacrylate was prepared with the use the Rayneri laboratory mixer until a homogeneous mixture is obtained.
4. The ingredients of the composition obtained by steps 1-3, were combined and stirred with the Rayneri laboratory mixer until a homogeneous mixture was obtained. An aluminum foil was positioned on the top of the container to prevent the solvents from evaporating.
5. The mixture was poured into a light-opaque flask in order to be protected from light.
6. Ethyl Trimethylbenzoylphenylphosphinate photoinitiator was added into the mixture of the opaque bottle and placed under stirring with the use of Rayneri laboratory mixer until a homogeneous mixture was obtained. An aluminum foil was used to cover the container in order to prevent the solvents from evaporation.

Top Coat:
1. All components of the composition were poured into the opaque flask and stirred with the Rayneri laboratory mixer until a homogeneous mixture was obtained.
2. An aluminum foil was used to cover the flask in order to prevent the solvents from evaporation.

Inventive compositions of the nail treatment system are represented but not limited by examples in Table 1, shown below.

TABLE 1

Exemplary Compositions

| INCI Name | Basecoat (% wt)* | Second coat (color coat) (% wt)* | Topcoat (optional) (% wt)* |
|---|---|---|---|
| tributyl citrate | 0.99 | | |
| violet 2 | | | 0.0004 |
| red 6 lake | | 0.58 | |
| titanium dioxide (and) oxidized polyethylene | | 0.24 | |
| red 7 lake | | 0.7 | |
| dipropylene glycol dibenzoate | 6.22 | | |
| trimethyl hydroxypentyl isobutyrate | 1.26 | | |
| stearalkonium hectorite | | 0.5 | |
| lithium magnesium sodium silicate | 0.1 | | |
| silica (and) polyethylene | 0.9 | | |
| cellulose acetate butyrate | | 0.4 | |
| styrene/acrylates copolymer | 4.9 | | |
| butyl acetate (and) acrylates copolymer | | 2 | 2 |
| polyurethane-34 | 2.6 | | |
| ethyl trimethylbenzoyl phenylphosphinate | | 4 | 4 |
| ammonium acrylates copolymer | 20.3 | | |
| peg 400 extended urethane dimethacrylate -P2 | | 5 | |
| styrene/acrylates/ammonium methacrylate copolymer | 49.82 | | |
| urethane dimethacrylate-P2 | | 14.06 | 13.2196 |
| isophorone urethane dimethacrylate -P1 | | 51.22 | 60.22 |
| tetrahydrofurfuryl methacrylate | | 21.3 | 20.56 |
| phenoxyethanol | 0.65 | | |
| water | 9.9 | | |
| caprylyl glycol | 0.85 | | |
| propylene glycol butyl ether (and) propylene glycol butyl ether | 1.51 | | |

(% wt)* Overall weight of individual components present in the composition.

Evaluation of Inventive Compositions: Methods and Results
The inventive compositions were compared for various properties against the following comparator formulations:
Comparator A:
Topcoat:
DI-HEMA TRIMETHYLHEXYL DICARBAMATE, HEMA, Hydroxypropyl methacrylate, ethyl trimethylbenzoyl phenylphosphinate, hydroxycyclohexyl phenyl ketone, CI 60725/Violet 2, Methyl diethanolamine
Color Coat:
Di-Hema Trimethylhexyl dicarbamate, HEMA, hydroxypropyl methacrylate, Ethyl Trimethylbenzoyl phenylphosphinate, clay, PEG-9 Dimethacrylate, polyethylene terephthalate, hydroxycyclohexyl phenyl ketone, Bis(glycidoxyphenyl)propane/Bisaminomethylnorbornane copolymer, isobutylphenoxy epoxy resin, silica, synthetic fluorphlogopite, polyurethane-11, aluminum hydroxide, polyurethane-33, Tin oxide, pigments.
Basecoat:
Alcohol denat., Butyl Acetate, Di-HEMA Trimethylhexyl dicarbamate, Ethyl acetate, Heptane, Nitrocellulose, Tosylamide/Epoxy Resin, Isobornyl Methacrylate, HEMA, Trimethyl pentanyl Diisobutyrate, Isopropyl Alcohol, Poluvinyl butyral, Ethyl Trimethylbenzoyl phenylphosphinate, Camphor, Acrylic Acid, Hydroxycyclohexyl Phenyl ketone, Dimehicone, CI60725/Violet 2, Tocopheryl acetate, Panthenol.
Comparator B:
Basecoat:
Tetrahydrofurfuryl Methacrylate, PPG-5 Methacrylate, Cellulose Acetate Butyrate, Isopropylidenediphenol PEG-2

Dimethacrylate, Acetone, Alcohol Denat., Acrylate Copolymer, Di-HEMA Trimethylhexyl Dicarbamate, Bis(Glyceryl Dimethacrylate) Pyromelliate, Hydrocyclhexyl Phenyl Ketone, Butyl Acetate, Ethyl Trimethylbenzoyl Phenylphosphinate, Phenyldimethoxyacetophenone, Hydroxypropyl Methacrylate Color Coat:
Butyl Acetate, Cellulose Acetate Butyrate, Aliphatic Urethane Methacrylate Oligomer, Polypropylene Glycol Monomethacrylate, Tetrahydrofurfuryl Methacrylate, Titanium dioxide, Mica, Di-HEMA Trimethylhexyl Dicarbamate, Phenyldimethoxyacetophenone, Hydroxycyclohexyl Phenyl Ketone, Drometrizole, Tin Oxide, Hydroxypropyl Methacrylate, Methyl Pyrrolidone, Silica, pigments Topcoat:
Cellulose Acetate Butyrate, Bis-HEMA Poly(1,4-Butanediol)-22/IPDI Copolymer, Di-HEMA Trimethylhexyl Dicarbamate, Tetrahydrofurfuryl Methacrylate, PPG-5 Methacrylate, Butyl Acetate, Ethyl Acetate, Ethyl Trimethylbenzoyl Phenylphosphinate, Diisobutyl Adipate, Hydropropyl Methacrylate, CD60730 (Ext. Violet 2)

In accordance with the invention, the color coat and topcoat of the inventive nail treatment system, contain Tetrahydrofurfuryl Methacrylate (THFMA) and urethane (meth)acrylate P1. In contrast, comparator B contains Tetrahydrofurfuryl Methacrylate (THFMA) and urethane (meth)acrylate (Di-HEMA Trimethylhexyl Dicarbamate) in all coats, while comparator A does not contain Tetrahydrofurfuryl Methacrylate in any of the coats, just urethane (meth)acrylate (Di-HEMA Trimethylhexyl Dicarbamate).

Methods of Nail Treatments (Applications) Using Inventive and Comparative Compositions.

Tests were conducted on different days, using the procedures summarized below in Table 2.

TABLE 2

| Inventive procedure | Comparative procedure A | Comparative procedure B | Comparative procedure C | Comparative procedure D | Comparative procedure E |
|---|---|---|---|---|---|
| Nail | Nail | Nail | Nail | Nail | Nail |
| 1 coat of inventive Basecoat | 2 coats of inventive Basecoat | 2 coats of inventive Basecoat | 1 coat of Comparator A basecoat | 2 coats of inventive Basecoat | 1 coat of Comparator B basecoat |
| — | 1 coat of primer* | — | — | — | — |
| 2 coats of inventive second (color) coat | 2 coats of comparator A color coat | 2 coats of comparator A color coat | 2 coats of comparator A color coat | 2 coats of comparator B color coat | 2 coats of comparator B color coat |
| inventive topcoat | comparator A top coat | comparator A top coat | comparator A Topcoat | comparator B Topcoat | comparator B Topcoat |

Primer*—UV polymerizable layer applied on the tips of nails between basecoat and color coat application, comprising: Ethyl acetate, 2,2-Bis-(4-(2-hydroxy-3-methacryloxypropoxy)BIS-GMA, 2-Hydroxy ethyl methacrylate.

The steps of treatments (applications of nail compositions) incorporating inventive and comparative compositions were conducted as per examples provided below.

TABLE 3

Detailed procedure of nail treatment with inventive compositions (inventive procedure) shown in Table 2.

| Steps of treatment | Order of treatment | Description of treatment |
|---|---|---|
| Nails preparation | 1 | Nails were buffed and wiped off with alcohol wipes. |
| Water-Based Basecoat | 2 | 1 layer of the inventive water-based basecoat was applied and dried for 1 min at ambient conditions. |
| Second Coat (Color Coat) | 3 | 1$^{st}$ layer of the inventive color coat composition was applied and cured for 30 s with LED Lamp. |
|  | 4 | 2$^{nd}$ layer of the inventive color coat composition was applied and cured for 30 s with LED Lamp. |
| Topcoat | 5 | 1 coat of the inventive topcoat was applied and cured for 1 min with LED Lamp. |
| Removal of tacky layer | 6 | The tacky layer present on the surface of the treated nails was removed with alcohol wipes. |

TABLE 4

Detailed procedure of nail treatment with inventive basecoat, primer and comparator A (procedure A) according to Table 2.

| Steps of treatment | Order of treatment | Description of treatment |
|---|---|---|
| Nails preparation | 1 | Nails were buffed and wiped off with alcohol wipes. |
| Water-Based Basecoat | 2 | 1$^{st}$ layer of the water-based basecoat was applied and dried for 1 min at ambient conditions. |
|  | 3 | 2$^{nd}$ layer of the water-based basecoat was applied and dried for 1 min at ambient conditions. |
| Primer | 4 | Primer* (as described above) was applied to the free edge of the nail plate and dried for 30 s at the ambient conditions (not UV or LED cured). |
| Color coat | 5 | 1$^{st}$ layer of the comparator A color coat was applied and cured for 30 s with LED Lamp. |
|  | 6 | 2$^{nd}$ layer of the comparator A color coat was applied and cured for 30 s with LED Lamp. |
| Topcoat | 7 | 1 coat of the comparator A topcoat was applied and cured for 1 min with LED Lamp. |

TABLE 4-continued

Detailed procedure of nail treatment with inventive basecoat, primer and comparator A (procedure A) according to Table 2.

| Steps of treatment | Order of treatment | Description of treatment |
| --- | --- | --- |
| Removal of tacky layer | 8 | The tacky layer present on the surface of the treated nails was removed with alcohol wipes. |

TABLE 5

Detailed procedure of nail treatment with inventive basecoat and comparator A (procedure B) according to Table 2.

| Steps of treatment | Order of treatment | Description of treatment |
| --- | --- | --- |
| Nails preparation | 1 | Nails were buffed and wiped off with alcohol wipes. |
| Water-Based Basecoat | 2 | $1^{st}$ layer of the water-based basecoat was applied and dried for 1 min at ambient conditions. |
|  | 3 | $2^{nd}$ layer of the water-based basecoat was applied and dried for 1 min at ambient conditions. |
| Color Coat | 4 | $1^{st}$ layer of the comparator A color coat was applied and cured for 30 s with LED Lamp. |
|  | 5 | $2^{nd}$ layer of the comparator A color coat was applied and cured for 30 s with LED Lamp. |
| Topcoat | 6 | 1 coat of the comparator A topcoat was applied and cured for 1 min with LED Lamp. |
| Removal of tacky layer | 7 | The tacky layer present on the surface of the treated nails was removed with alcohol wipes. |

TABLE 6

Detailed procedure of nail treatment with comparator A (procedure C) according to Table 2.

| Steps of treatment | Order of treatment | Description of treatment |
| --- | --- | --- |
| Nails preparation | 1 | Nails were buffed and wiped off with alcohol wipes. |
| Basecoat | 2 | 1 coat of the comparator A basecoat was applied and cured for 30 s with LED Lamp. |
| Color Coat | 3 | $1^{st}$ layer of the comparator A color coat was applied and cured for 30 s with LED Lamp. |
|  | 4 | $2^{nd}$ layer of the comparator A color coat was applied and cured for 30 s with LED Lamp. |
| Topcoat | 5 | 1 coat of the comparator A topcoat was applied and cured for 1 min with LED Lamp. |
| Removal of tacky layer | 6 | The tacky layer present on the surface of the treated nails was removed with alcohol wipes. |

TABLE 7

Detailed procedure of nail treatment with inventive basecoat and comparator B (procedure D) shown in Table 2.

| Steps of treatment | Order of treatment | Description of treatment |
| --- | --- | --- |
| Nails preparation | 1 | Nails were wiped off with alcohol wipes. |
| Water-Based Basecoat | 2 | $1^{st}$ layer of the water-based basecoat was applied and dried for 1 min at ambient conditions. |
|  | 3 | $2^{nd}$ layer of the water-based basecoat was applied and dried for 1 min at ambient conditions. |
| Color Coat | 4 | $1^{st}$ layer of the comparator B color coat was applied and cured for 2 minutes with UV Lamp. |
|  | 5 | $2^{nd}$ layer of the comparator B color coat was applied and cured for 2 minutes with UV Lamp. |
| Topcoat | 6 | 1 coat of the comparator B topcoat was applied and cured for 2 min with UV Lamp. |
| Removal of tacky layer | 7 | The tacky layer present on the surface of the treated nails was removed with alcohol wipes. |

TABLE 8

Detailed procedure of nail treatment with comparator B (procedure E) shown in Table 2.

| Steps of treatment | Order of treatment | Description of treatment |
| --- | --- | --- |
| Nails preparation | 1 | Nails were wiped off with alcohol wipes. |
| Basecoat | 2 | 1 coat of the comparator B basecoat was applied and cured for 10 s with UV Lamp. |
| Color Coat | 3 | $1^{st}$ layer of the comparator B color coat was applied and cured for 2 min with UV Lamp. |
|  | 4 | $2^{nd}$ layer of the comparator B color coat was applied and cured for 2 min with UV Lamp. |
| Topcoat | 5 | 1 coat of the comparator B topcoat was applied and cured for 2 min with UV Lamp. |
| Removal of tacky layer | 6 | The tacky layer present on the surface of the treated nails was removed with alcohol wipes. |

TABLE 9

Removal instructions of compositions applied according to procedures shown in Tables 4, 5 and 7.

| Order of removal procedure | Steps of removal procedure |
| --- | --- |
| 1 | Hands were soaked in warm water (40 C.) or warm water with surfactant (soap) mixture for 5 min. |
| 2 | Loosened edge of the inventive nail treatment system (near cuticle or free edge, whichever easier) was pushed with a cuticle pusher and peeled off from the surface of nail. Nails were re-soaked in warm water if necessary to aide in removal. |
| 3 | Cuticle oil was applied on nails. |

TABLE 10

Removal instructions of compositions applied according to procedures shown in Table 6.

| Order of removal procedure | Steps of removal procedure |
| --- | --- |
| 1 | Cotton swab was soaked in acetone, placed on nail and wrapped with foil. |
| 2 | After 15 minutes the foil was removed. |
| 3 | Remaining polish was pushed off the nails with orangewood stick. |
| 4 | Cuticle oil was applied on nails. |

TABLE 11

Removal instructions of compositions applied according to procedures shown in Table 8.

| Order of removal procedure | Steps of removal procedure |
| --- | --- |
| 1 | Cotton swab was soaked in acetone, placed on nail and wrapped with foil. |
| 2 | After 10 minutes the foil was removed. |
| 3 | Remaining polish was pushed off the nails with orangewood stick. |
| 4 | Cuticle oil was applied on nails. |

TABLE 12

Removal instructions of compositions applied according to procedures shown in Table 3 (Inventive procedure).

| Order of removal procedure | Steps of removal procedure |
| --- | --- |
| 1 | Hands were soaked in warm water (40 C.) or warm water with surfactant (soap) mixture for 1 min. |
| 2 | Loosened edge of the inventive nail treatment system (near cuticle or free edge, whichever easier) was pushed off with a cuticle pusher and peeled off from the surface of nail. Nails were re-soaked in warm water if necessary to aide in removal. |
| 3 | Cuticle oil was applied on nails. |

TABLE 13

Results of Consumer Tests

| | Wear at 14 days | Removal | Nail conditions after removal |
| --- | --- | --- | --- |
| Inventive procedure | ♦♦♦♦ | ♦♦♦♦ | ♦♦♦♦ |
| Comparative procedure A | ♦♦♦ ½♦ | ♦♦♦♦ | ♦♦♦♦ |
| Comparative procedure B | ♦♦♦ | ♦♦♦♦ | ♦♦♦♦ |
| Comparative procedure C | ♦♦♦♦ | ♦♦♦ | ♦♦♦ |
| Comparative procedure D | ♦♦♦ | ♦♦♦ | ♦♦♦ ½♦ |
| Comparative procedure E | ♦♦♦♦ | ♦♦♦ ½♦ | ♦♦♦ |

In the above table, the greater number of ♦ means the better performance in each of the tested categories.

The inventive and comparative nail treatments were evaluated through consumer tests encompassing eight to twelve panelists for each test. The tested compositions according to inventive procedure and comparative procedures A, B, C, D and E (as described above) were applied by professional cosmetologists (manicurists). Each panelist tested two different products at the same time. One product was applied on one hand; the second was tested on the other hand. Wear was monitored for the length of 14 days. At the 14$^{th}$ day of wear the removal procedures were conducted (as described above). The observations of wear, removal and nail conditions were completed by professional manicurists.

It was observed by the manicurists that at the 14$^{th}$ day of the studies, the inventive procedure which involved application of a single layer of the inventive basecoat and the second coat (color coat) and/or topcoat, both containing Tetrahydrofurfuryl Methacrylate (THFMA) and urethane methacrylate oligomer (second coat and topcoat as described above), resulted in parity of wear with the comparative procedures C and E, and better/improved wear in comparison to the comparative procedures A, B and D.

The comparative procedures C and E included application of commercially available UV gel nail products (as described above) which require UV or LED curing (polymerization) of each layer of every coat applied on nails. In contrast, the other comparative procedures (A, B and D) involved two applications of the inventive basecoat. In addition, the comparative procedure D included application of the comparative color coat and topcoat which contained Tetrahydrofurfuryl Methacrylate (THFMA) and urethane methacrylate, while comparative procedures A and B involved application of products without Tetrahydrofurfuryl Methacrylate (THFMA).

As is shown in Table 13, removal of the nail treatment according to the inventive procedure, performed better than the comparative procedures C and E and it was at parity with the comparative procedures A, B and D.

Further, it was noted that after removal of the inventive nail treatment applied according to the inventive procedure, the nails looked healthier (glossy and moisturized) in comparison to the nails being treated with the procedure C and E. Also, they appeared in slightly better condition than the nails treated according to the procedure D. It was also observed that the healthy appearance of the nails treated with the inventive procedure/compositions was at parity with the nails treated according to the comparative procedures A and B.

What is claimed is:

1. A nail treatment system comprising:
   (1) at least one non-UV curable basecoat comprising:
      water; and
      at least one non-UV curable latex; and
   (2) at least one UV curable second coat comprising:
      at least one photocrosslinkable urethane (meth)acrylate compound P1;
      at least one (meth)acrylate monomer; and
      at least one photoinitiator,
   wherein when the nail treatment system is applied to nails and subjected to photocrosslinking, the resulting nail coating is removable with warm, soapy water and
   wherein the at least one (meth)acrylate monomer in the second coat penetrates the basecoat.

2. The nail treatment system of claim 1, wherein the UV curable second coat comprises:
   at least one photocrosslinkable urethane (meth)acrylate compound P1 comprising at least one structural unit:

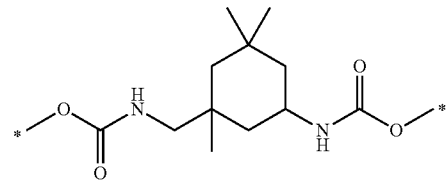

at least one (meth)acrylate monomer;
at least one photoinitiator;
optionally at least one photocrosslinkable urethane (meth) acrylate compound P2;
optionally at least one film-forming polymer P3;
optionally at least one coloring agent; and
optionally at least one solvent.

3. The nail treatment system of claim 1, which comprises:
(1) at least one non-UV curable basecoat comprising:
water;
at least one non-UV curable adhesive latex;
optionally at least one plasticizer;
optionally at least one coalescent;
optionally at least one abrasive agent; and
(2) at least one UV curable second coat comprising:
at least one photocrosslinkable urethane (meth)acrylate compound P1 comprising at least one structural unit:

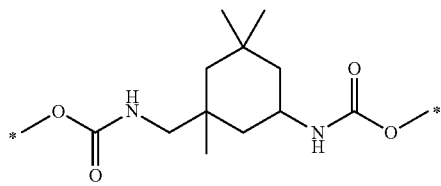

at least one (meth)acrylate monomer;
at least one photoinitiator;
optionally at least one photocrosslinkable urethane (meth)acrylate compound P2;
optionally at least one film-forming polymer P3;
optionally at least one coloring agent; and
optionally at least one solvent;
wherein the ratio of at least one photocrosslinkable urethane (meth)acrylate compound P1 to at least one methacrylate monomer is greater than or equal to about 1:1, by weight.

4. The nail treatment system of claim 3 wherein the at least one non-UV curable adhesive latex is at least one aqueous acrylate copolymer dispersion.

5. The nail treatment system of claim 4 wherein the at least one non-UV curable adhesive latex is present in an amount of from about 5% to about 95%, by weight, relative to the total weight of the non-UV curable basecoat.

6. The nail treatment system of claim 5 wherein the water is present in an amount of from about 10% to about 95%, by weight, relative to the total weight of the non-UV curable basecoat.

7. The nail treatment system of claim 6 wherein the at least one non-UV curable basecoat further comprises at least one plasticizer in an amount from about 0.1% to about 25%, by weight, relative to the total weight of the non-UV curable basecoat.

8. The nail treatment system of claim 7 wherein the at least one UV curable second coat further comprises at least one photocrosslinkable urethane (meth)acrylate compound P2 in an amount from about 1% to about 80%, by weight, relative to the total weight of the UV curable second coat.

9. The nail treatment system of claim 8 wherein the at least one UV curable second coat further comprises at least one film-forming polymer P3 in an amount from about 0.2% to about 10%, by weight, relative to the total weight of the UV curable second coat.

10. The nail treatment system of claim 1 comprising:
(1) at least one non-UV curable basecoat comprising:
water present in an amount from about 30% to about 90% by weight;
at least one non-UV curable adhesive latex in an amount from about 10% to about 90% by weight;
at least one plasticizer in an amount from about 1% to about 10% by weight;
at least one coalescent in an amount from about 1% to about 20% by weight; and
at least one abrasive agent in an amount from about 0.1% to about 5% by weight; and
(2) at least one UV curable second coat comprising:
at least one photocrosslinkable urethane (meth)acrylate compound P1 comprising at least one structural unit:

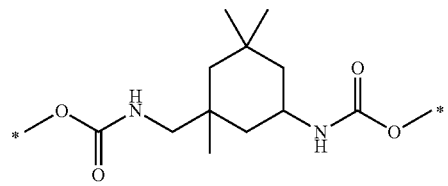

in an amount from about 5% to about 80% by weight;
at least one (meth)acrylate monomer in an amount from about 5% to about 30% by weight;
at least one photoinitiator in an amount from about 1% to about 10% by weight;
at least one photocrosslinkable urethane (meth)acrylate compound P2 in an amount from about 5% to about 70% by weight;
at least one film-forming polymer P3 in an amount from about 0.2% to about 10% by weight;
at least one coloring agent in an amount from about 0.1% to about 5% by weight; and
at least one solvent from about 0.5% to about 10% by weight;
wherein the ratio of at least one photocrosslinkable urethane (meth)acrylate compound P1 to at least one (meth)acrylate monomer is greater than or equal to 1:1, by weight.

11. A nail treatment system comprising:
(1) at least one non-UV curable basecoat comprising:
water present in an amount from about 30% to about 90% by weight;
at least one non-UV curable adhesive latex in an amount from about 10% to about 95% by weight;
at least one plasticizer in an amount from about 1% to about 10% by weight;
optionally at least one coalescent in an amount from about 1% to about 20% by weight; and
optionally at least one abrasive agent in an amount from about 0.1% to about 5% by weight; and
(2) at least one UV curable second coat comprising:
at least one photocrosslinkable urethane (meth)acrylate compound P1 comprising at least one structural unit:

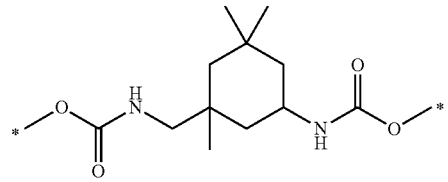

in an amount from about 5% to about 80% by weight;
at least one (meth)acrylate monomer in an amount from about 5% to about 30% by weight;
at least one photoinitiator in an amount from about 1% to about 10% by weight;
at least one photocrosslinkable urethane (meth)acrylate compound P2 in an amount from about 5% to about 70% by weight;

at least one film-forming polymer P3 in an amount from about 0.2% to about 10% by weight;
optionally at least one coloring agent in an amount from about 0.1% to about 5% by weight; and
optionally at least one solvent from about 0.5% to about 10% by weight;
wherein the ratio of at least one photocrosslinkable urethane (meth)acrylate compound P1 to at least one methacrylate monomer is from about 1.5:1 to about 5:1, by weight,
wherein when the nail treatment system is applied to nails and subjected to photocrosslinking, the resulting nail coating is removable with warm, soapy water and
wherein the at least one (meth)acrylate monomer in the second coat penetrates the basecoat.

12. The nail treatment system of claim 11 wherein the at least one non-UV curable adhesive latex is selected from acrylic copolymers, (meth)acrylic copolymers, polyurethanes and mixtures thereof.

13. The nail treatment system of claim 12 wherein the at least one (meth)acrylate monomer is present in an amount from about 10% to about 25%, by weight, relative to the total weight of the UV curable second coat.

14. The nail treatment system of claim 1 wherein the at least one UV curable second coat further comprises pigment.

15. A method of making up or enhancing the appearance of the nails comprising applying to the nails a nail treatment system comprising:
(1) at least one non-UV curable basecoat comprising:
water present in an amount from about 30% to about 90% by weight;
at least one non-UV curable adhesive latex in an amount from about 10% to about 95% by weight;
at least one plasticizer in an amount from about 1% to about 10% by weight;
optionally at least one coalescent in an amount from about 1% to about 20% by weight; and
optionally at least one abrasive agent in an amount from about 0.1% to about 5% by weight; and
(2) at least one UV curable second coat comprising:
at least one photocrosslinkable urethane (meth)acrylate compound P1 comprising at least one structural unit:

in an amount from about 5% to about 80% by weight;
at least one (meth)acrylate monomer in an amount from about 5% to about 30% by weight;
at least one photoinitiator in an amount from about 1% to about 10% by weight;
at least one photocrosslinkable urethane (meth)acrylate compound P2 in an amount from about 5% to about 70% by weight;
at least one film-forming polymer P3 in an amount from about 0.2% to about 10% by weight;
at least one coloring agent in an amount from about 0.1% to about 5% by weight; and
optionally at least one solvent from about 0.5% to about 10% by weight;
wherein the ratio of at least one photocrosslinkable urethane (meth)acrylate compound P1 to at least one methacrylate monomer is from about 1.5:1 to about 5:1, by weight; and
(3) optionally at least one topcoat,
wherein when the nail treatment system is applied to nails and subjected to photocrosslinking, the resulting nail coating is removable with warm, soapy water and
wherein the at least one (meth)acrylate monomer in the second coat penetrates the basecoat.

16. A kit for a nail treatment system for treating nails comprising:
(1) a container containing at least one non-UV curable basecoat comprising:
water present in an amount from about 30% to about 90% by weight;
at least one non-UV curable adhesive latex in an amount from about 10% to about 95% by weight;
at least one plasticizer in an amount from about 1% to about 10% by weight;
optionally at least one coalescent in an amount from about 1% to about 20% by weight; and
optionally at least one abrasive agent in an amount from about 0.1% to about 5% by weight; and
(2) a second container containing at least one UV curable second coat comprising:
at least one photocrosslinkable urethane (meth)acrylate compound P1 comprising at least one structural unit:

in an amount from about 5% to about 80% by weight;
at least one (meth)acrylate monomer in an amount from about 5% to about 30% by weight;
at least one photoinitiator in an amount from about 1% to about 10% by weight;
at least one photocrosslinkable urethane (meth)acrylate compound P2 in an amount from about 5% to about 70% by weight;
at least one film-forming polymer P3 in an amount from about 0.2% to about 10% by weight;
at least one coloring agent in an amount from about 0.1% to about 5% by weight; and
optionally at least one solvent from about 0.5% to about 10% by weight; and
(3) optionally a third container containing at least one topcoat, wherein when the nail treatment system is applied to nails and subjected to photocrosslinking, the resulting nail coating is removable with warm, soapy water and wherein the at least one (meth)acrylate monomer in the second coat is capable of penetrating the basecoat.

* * * * *